US011160766B2

(12) United States Patent
Grentzmann

(10) Patent No.: US 11,160,766 B2
(45) Date of Patent: Nov. 2, 2021

(54) PERITONEAL THERAPEUTIC FLUID

(71) Applicant: OPTERION Health AG, Kehrsiten (CH)

(72) Inventor: Guido Grentzmann, Hamburg (DE)

(73) Assignee: OPTERION HEALTH AG, Kehrsiten (CH)

( * ) Notice: Subject to any disclaimer, the term of this patent is extended or adjusted under 35 U.S.C. 154(b) by 0 days.

(21) Appl. No.: 16/586,113

(22) Filed: Sep. 27, 2019

(65) Prior Publication Data
US 2020/0022926 A1 Jan. 23, 2020

Related U.S. Application Data

(62) Division of application No. 15/745,903, filed as application No. PCT/EP2016/067186 on Jul. 19, 2016, now abandoned.

(30) Foreign Application Priority Data

Jul. 20, 2015 (EP) .................................. 15177544

(51) Int. Cl.
A61K 31/05 (2006.01)
A61K 47/10 (2017.01)
A61K 47/26 (2006.01)
A61K 47/36 (2006.01)
A61M 1/28 (2006.01)

(52) U.S. Cl.
CPC .............. A61K 31/05 (2013.01); A61K 47/10 (2013.01); A61K 47/26 (2013.01); A61K 47/36 (2013.01); A61M 1/287 (2013.01); A61M 2202/0021 (2013.01)

(58) Field of Classification Search
CPC ........ A61K 31/05; A61K 47/10; A61K 47/26; A61K 47/36; A61M 1/287; A61M 2202/0021; A61P 41/00; A61P 43/00; A61P 7/08
See application file for complete search history.

(56) References Cited

U.S. PATENT DOCUMENTS

| 6,841,578 | B2 | 1/2005 | Sonis |
| 8,431,617 | B2 | 4/2013 | Garaci et al. |
| 9,919,004 | B2 | 3/2018 | Kizhakkedathu et al. |
| 2005/0182026 | A1 | 8/2005 | Hills et al. |
| 2005/0182086 | A1 | 8/2005 | Defossa et al. |
| 2006/0292099 | A1 | 12/2006 | Milburn et al. |
| 2009/0035240 | A1 | 2/2009 | Maes et al. |
| 2009/0162457 | A1 | 6/2009 | Minegishi et al. |
| 2011/0281957 | A1* | 11/2011 | Kuhrts .................. A61K 31/05 514/733 |
| 2014/0199391 | A1 | 7/2014 | Barbara |
| 2015/0141512 | A1* | 5/2015 | Kizhakkedathu ......... A61P 7/00 514/561 |

FOREIGN PATENT DOCUMENTS

| EP | 2774915 A1 | 9/2014 |
| JP | 2005526014 A | 9/2005 |
| JP | 2015515481 A | 5/2015 |
| RU | 2158593 C2 | 11/2000 |
| WO | 0128544 A2 | 4/2001 |
| WO | 0222188 A1 | 3/2002 |
| WO | 2005049049 A1 | 6/2005 |
| WO | 2006019855 A1 | 2/2006 |
| WO | 2009017866 A1 | 2/2009 |

OTHER PUBLICATIONS

Sogutlu et al. (Cell Biochemistry and Function, 2007, 25, 217-220) (Year: 2007).*
Ceelen (Nature Reviews, 7, Feb. 2010, p. 108-115) (Year: 2010).*
Tufts (https://www.tuftsmedicalcenter.org, Jul. 2014) (Year: 2014).*
Kitada et al. (Oxidative Medicine and Cellular Longevity, 2013, p. 1-7). (Year: 2013).*
Barre, et al.: "Decreased In Vitro Formation fo AGEs with Extraneal Solution Coppared to Dextrose-Containihng Peritoneal Dialysis Solutions", Adv. Perit. Dial. (1999) 15:12-6.
Catalan, et al.: Acceleration of Neutrophil Apoptosis by Glucose-Containing Peritoneal Dealysis Solutions: Role of Caspases, J. Am. Soic. Nephrol. 12 (2001), pp. 2442-2449.
Jun, et al.: "Effect of Resveratrol of Reactive Oxygen Species in Human Peritoneal Mesothelial Cells Exposed to Glucose-based Peritoneal Dialysis", J. Med. Res. 42(11) (2013), pp. 43-46.
Kitamura, et al.: "Epigallocatechin gallate suppresses peritoneal fibrosis in mice", Chemico-Biological Interactions 195 (2012), pp. 95-104.
Konings, et al.: "Influence of Icodextrin on Plasma and Dialysate Levels of Ne_(Carboxymethyl)Lysisne and Ne_(Carboxyethyl)Lysine", Peritoneal Dialysis International 25 (2005), pp. 591-595.
Lee, et al.: "The monocyte chemoattractant protein-1 (MCP-1)/CCR2 system is involved in peritoneal dialysis-mesenchymal transition of peritoneal-mesenchymal cells", Laboratory Ivestigation 92 (2012), pp. 1698-1711.
Mangram, et al.: "Outbreak of sterile peritonitis among continuous cycling peritoneal dialysis patients", Kidney International 54 (1998), pp. 1367-1371.
Moriishi and Kawanishi: "Icodextrin and Intraperitoneal Inflammation", Peritoneal Dialysis International 28 (2008), Suppl. 3, pp. S96-S100.
Park, et al.: "Effect of Glucose Degradation Products on the Peritoneal Membrane in a Chronic Inflammatory Infusion Model of Peritoneal Dialysis in the Rat", Peritoneal Dialysis International 24 (2004), pp. 115-122.
Pezzuto, et al.: "Resveratrol derivatives: a patent review (2009-2012)", Expert Opin.Ther. Patents 23(12) (2013), pp. 1529-1546.
Wee, et al.: "The new peritoneal dialysis solutions: friends only, or foes in part?", Nature Clinical Practice Nephrology 3(11), (2007), pp. 604-612.

(Continued)

Primary Examiner — Umamaheswari Ramachandran
(74) Attorney, Agent, or Firm — Arent Fox LLP

(57) ABSTRACT

Peritoneal therapeutic fluid comprising one or more of a biocompatibility enhancing agent (BCA) that is selected from the group consisting of a polyphenolic compound, a metabolite of a polyphenolic compound which is obtained by metabolization in the human or animal body, a salt or a glycoside of a polyphenolic compound.

55 Claims, 9 Drawing Sheets

(56) References Cited

OTHER PUBLICATIONS

Williams, et al.: "Morphologic Changes in the Peritoneal Membrane of Patients with Renal Disease", J. Am. Soc. Nephrol. 13 (2002), pp. 470-479.
Xu, et al.: "Manual of New and Complete Practical Drugs", Henan Science and Technology Press (2006), p. 1349.
Zweers, et al.: "Vascular endothelial growth factor in peritoneal dialysis, a longitudinal follow-up", J. Lab. Clin, MEd. 137(2) (2001), pp. 125-132, http://dare.uva.nl.
Boehm, et al.: "Cellular stress-response modulators in the acute rat model of peritoneal dialysis", Pediatr. Nephrol. 25 (2010), pp. 169-172.
Riesenhuber, et al.: "Quercetin protects human mesothelial cells against exposure to peritoneal dialysis fluid", Pediatr. Nephrol. 22 (2007), pp. 1205-1208.
Himedia Technical Data. Phosphate Buffered Saline, pH 7.2; M1452 (2011).
Marier, et al.: "Metabolism and Disposition of Resveratrol in Rats: Extent of Absorption, Glucoronidation, and Enterohepatic Recirculation Evidenced by a Linked-Rat Model", J. of Pharmacol, and Experim. Therapeutics, 302 (1) (2002), pp. 369-373.
Scholar Chemistry, Material Data Sheet: Physiolgical Saline Solution (2009), pp. 1-2.
Extraneal (Extraneal Product Information), (2014), pp. 1-13.
Stavenuiter, et al.: "Angiogenesis in Peritoneal Dialysis", Kidney Blood Press Res. 34 (2011), pp. 245-252.
Francioso, et al.: "Improved Stability of trans-Resveratrol in Aqueous Solutions by Carboxymethylated (1,3/1,6)-β-D-Glucan", Agricultural & Food Chem., 62 (2014), pp. 1520-1525.
Zhang, et al.: "Amino Acid-PEGylated Resveratrol and its Influence on Solubility and the Controlled Release Behaviour", Biol. Pharm. Bull. 37 (5), (2014), pp. 785-793.
Tang Zhihuan et al.: "Reactive oxygen species and high glucose induce growth inhibition of human peritoneal mesothelial cells through arresting cell cycle progression", Chinese Journal of Nephrology, vol. 19, No. 4 (2003), pp. 223-228.

\* cited by examiner

PERITONEAL THERAPEUTIC FLUID

This application is a division of U.S. patent application Ser. No. 15/745,903 filed Jan. 18, 2018, which is a § 371 of PCT/EP2016/067186 filed Jul. 19, 2016, and claims priority under Section 119 from EP 15 177 544.2 filed Jul. 20, 2015, each of which is hereby incorporated by reference in its entirety.

The present invention relates to a peritoneal therapeutic fluid showing increased biocompatibility.

Different peritoneal therapies encompass peritoneal nutrition, peritoneal dialysis, peritoneal detoxification in case of liver failure or drug abuse, treatment of primary and secondary peritoneal cancer, treatment of peritoneal infections and peritonitis, pre- or post-operative peritoneal treatment, or simply peritoneal administration of systemic treatments. They are carried out by applying peritoneal therapy fluids to the peritoneum.

Such fluids contain active pharmaceutical ingredients (APIs) and compounds to establish physiological osmotic pressure. Commonly applied compounds to achieve physiological osmotic pressure in peritoneal therapy fluids are the same as those that are used as osmotic agents in the case of dialysis, at concentrations between 0.5 and 20%, such as salts, mono- or oligo-saccharides such as glucose and glucose-oligomers or other saccharides, aminoacid mono- or multimers, PEGs or proteins, derivatives and/or compositions thereof.

Peritoneal dialysis (PD) is the most common peritoneal therapy applied to patients. It is a form of dialysis, representing an alternative to extra-corporal hemodialysis (HD). It has the advantage of being independent from heavy instrumentation, and can be done at home. The process uses the patient's highly capilarized peritoneum in the abdomen as a membrane across which fluids and dissolved substances (electrolytes, urea, glucose and other small molecules) are exchanged from the blood. To do so, peritoneal dialysis fluid is introduced through a permanent tube in the abdomen and flushed out either every night while the patient sleeps (automatic peritoneal dialysis) or via regular exchanges throughout the day (continuous ambulatory peritoneal dialysis). The specificity of Peritoneal dialysis lies in the fact that the compound(s) that establish osmotic pressure represent at the same time the active pharmaceutical ingredient(s), since the goal of peritoneal dialysis is to eliminate fluid and waste products out of the blood into the peritoneal dialysate.

Currently available peritoneal dialysis fluids (PDFs) cause cyto-toxicity due to high glucose concentration, glucose uptake from dialysate, the presence of glucose degradation products (GDPs), a low pH and supra-physiologic concentrations of lactate buffer. Bacterial "by-products" (Mangram et al. 1998) and infectious complications lead to inflammatory reactions (ter Wee et al. 2007). All these side-effects lead to fibrosis of the peritoneum, decreasing its dialysis efficiency over the long term. But even in absence of infections or inflammatory responses, significant fibrotic activity in the peritoneum of PD-patients may be observed (Reimold et al. 2013). In vitro studies have shown cytotoxicity of dialysis solutions on peritoneal mesothelial cells (Ha et al. 2000), which could be attributed to high osmolality, low pH, and GDPs.

GDPs form during heat sterilization of glucose containing solutions. Comparable degradation products form when heating any kind of sugar containing solutions. GDP formation during heat sterilization is greatly reduced, although not completely avoided, at acidic pH. Therefore, first generation PD solution are equilibrated at ph5 to 6, since GDP generation is reduced, and such a pH may be rapidly equilibrated in the patient's peritoneum. Lowest GDP formation occurs at pH3 to 3.5. Therefore second generation PD solutions are supplied as two compartment application, one containing a glucose solution at pH 3 to 3.5, the second compartment containing salts and buffers to establish a pH neutral solution by mixing the two compartments, shortly before application to peritoneal dialysis. GDPs or comparable degradation products may form advanced glycation end products (AGEs), which are carbohydrated proteins. AGEs are thought to be a factor in aging, vascular complications, diabetes mellitus and inflammation.

A way to address high glucose concentrations of PDFs is the use of maltodextrins as alternative osmotic agents to glucose. Icodextrin is such a maltodextrin derived from starch; it is a mixture of glucose polymers used as a colloidal solution in PDFs. Icodextrin-containing iso-osmolar PDFs are marketed under the trade name "Extraneal" (Baxter, USA). It is supplied under acidic pH, and significant elevation in PDF levels was detected in overnight effluent of PD patients, 6 months after the switch to icodextrin PDF (Moriishi et al. 2008).

As the prior art shows, there is still a significant need for reducing side-effects of dialysis treatments. A reduction of general cytotoxicity would potentially decrease long term fibrosis, keep the peritoneum efficacious for dialysis, and thereby prolonge average peritoneal dialysis therapy time windows in the long run.

SUMMARY OF THE INVENTION

The present invention provides with a peritoneal therapeutic fluid and a container or kit as defined in the claims and in the following description.

A peritoneal therapeutic fluid is disclosed, containing one or several biocompatibility enhancing agents (BCA). BCA may be characterized by reducing human peritoneal mesothelial cell-toxicity or peritoneal cell-toxicity. The peritoneal therapeutic fluid of the present invention can be used for the aforementioned purposes and other purposes mentioned in this description.

Preferred BCAs are polyphenolic compounds or derivatives of polyphenolic compounds.

Particularly suitable polyphenolic compounds are Resveratrol and Piceid (Polydatin). Particularly these compounds show a cell-viability increasing effect, rescuing human peritoneal mesothelial cells (HPMC) from PDF induced cytotoxicity.

The present invention provides a peritoneal therapeutic fluid comprising one or more BCAs, selected from the group consisting of a polyphenolic compound, a metabolite of a polyphenolic compound which is obtained by metabolization in the human or animal body, a salt of a polyphenolic compound, preferably a pharmaceutically acceptable salt, or a glycoside of a polyphenolic compound or a derivative of such compounds.

Further BCAs according to the invention are polyethylene glycol (PEG), or a derivative of a polyethylene glycol, such as mPEG.

Some derivatives are specified on the example of resveratrol. A salt of a polyphenolic compound is obtained be deprotonation of a polyphenolic compound at one or more phenolic hydroxy-groups.

Aforementioned BCA is also called a "cytotoxicity reducing compound", a "cytotoxicity reducing agent" or a "cell-toxicity reducing compound", or simply "a (first) compound".

So, in the present claims, the BCA can also be called a "compound". The term "cytotoxicity reducing" and "cell-toxicity reducing" were explained in more detail above in connection with the term BCA. "Cytotoxicity reducing" preferably means that a peritoneal therapeutic fluid of the invention shows lower cytotoxicity than a peritoneal therapeutic fluid not comprising the cytotoxicity reducing compound of the invention, and preferably having the same composition of other ingredients as the PTF of the invention. Particularly, a peritoneal therapeutic fluid of the invention shows higher viability of cells, preferably of human peritoneal mesothelial cells, in comparison to a peritoneal therapeutic fluid not comprising the cytotoxicity reducing compound of the invention.

A preferred glycoside is a glucoside. In a glucoside, a glucose moiety is bound to the polyphenolic compound, preferably via a hydroxyl group.

The BCA, particularly a polyphenolic compound, in the peritoneal therapeutic fluid may be selected from the group of stilbenoids, phenolic acids, and flavonoids.

Stilbenoids are naturally occurring substances corresponding to the structure C6-C2-C6, preferably polyphenols or polyphenol derivatives, belonging to the family of phenylpropanoids. Well studied Stilbenes are resveratrol (trans-3,5,4'-trihydroxystilbene), pinosylvine, piceatannol, pterostilbene, and a glycoside, piceid (resveratrol-3-O-β-mono-D-glucoside, also named as trans-3,5,4'-trihydroxystilbene-3-O-β-D-glucopyranoside).

In a specific embodiment, the BCA, preferably the polyphenolic compound, is selected from resveratrol, a resveratrol derivative, dihydro-resveratrol, and a glycoside thereof, such as astringin, piceid (polydatin), piceatannol, pterostilbene, piceid glucoside.

These compounds are specific, but non limiting examples for stilbenoides. In piceid glucoside, at least one further glucose moiety is bound to resveratrol via another hydroxyl group, i.e. the 5-hydroxylgroup and/or the 4'-hydroxylgroup of piceid.

In a further specific embodiment, the BCA, preferably the polyphenolic compound, is caffeic acid, which is a specific, but non limiting example for a phenolic acid.

In a further specific embodiment, the BCA, preferably the polyphenolic compound, is selected from luteolin or delphinidin, which are specific, but non limiting examples for a flavonoid.

Resveratrol derivatives are for example described in John M Pezzuto et al., Resveratrol derivatives: a patent review (2009-2012), Expert Opin. Ther. Patents (2013) 23 (12).

A resveratrol-derivative may be selected from the following compounds:

1

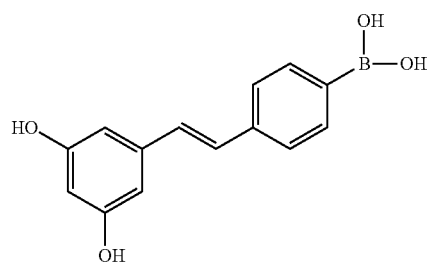

2

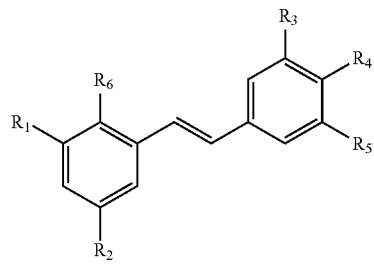

3

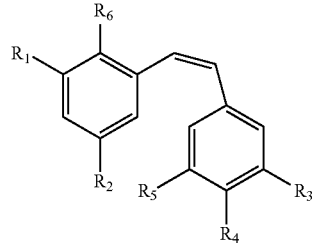

4

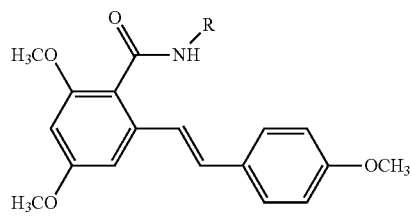

5

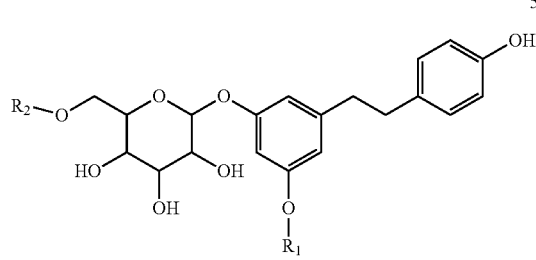

6

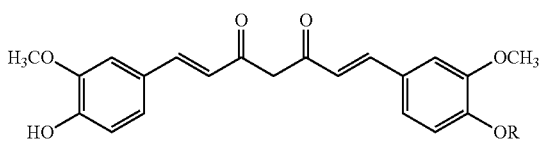

7

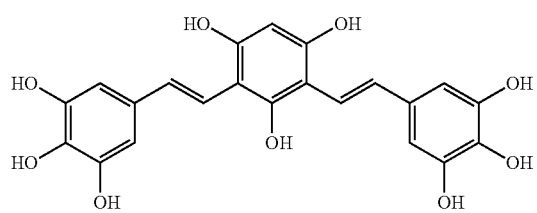

8

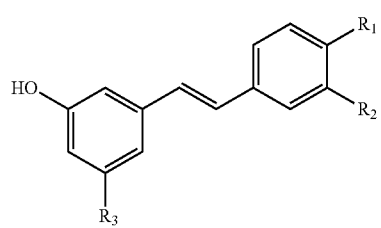

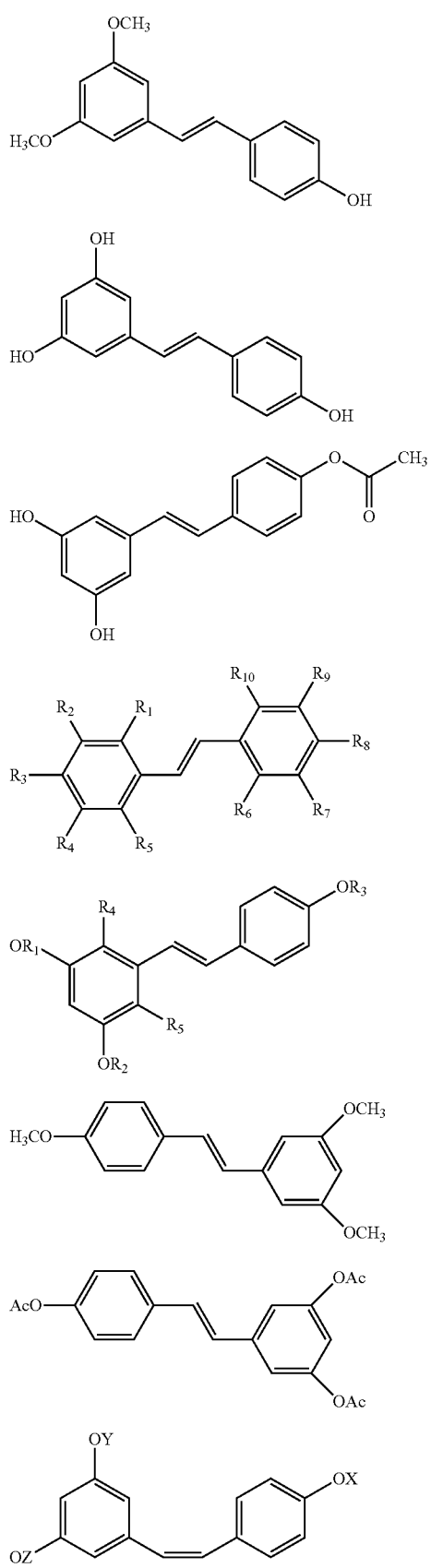
wherein in compound 2 and compound 3
R1=R2=R4=OH, R3=R5=R6=H; or
R1=R2=R4=OCH3, R3=R5=R6=H; or
R1=R2=R4=OCH3, R3=R5=H; R6=OH; or
R1=R2=R3=R5=OCH3, R4=R6=H; or
R1=R2=R3=R5=OCH3, R4=H, R6=OH; or
R1=R2=R3=R4=OCH3, R5=R6=H; or
R1=R2=R3=R4=OCH3, R5=H, R6=OH.
wherein in compound 4 R is one of the following moieties:
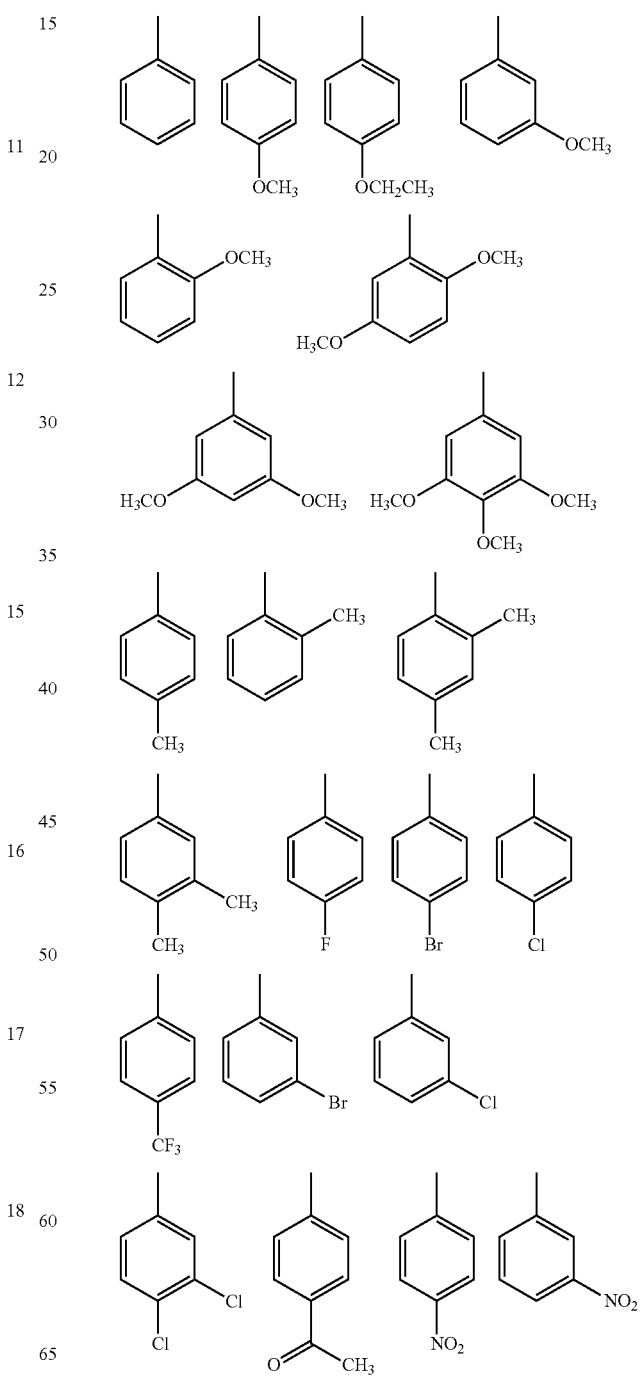

-continued
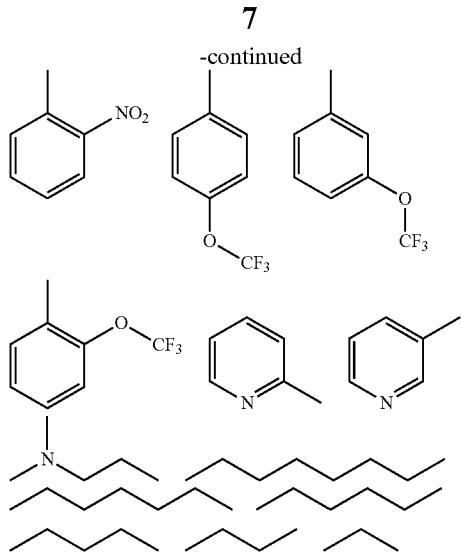
wherein in compound 5
R1 is hydrogen or a group of formula
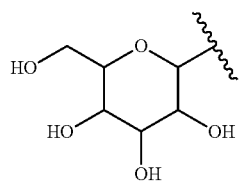 [SMILES: *C1OC(CO)C(O)C(O)C1O]
R2 is hydrogen or forms together with the oxygen to which it is bound an acyl group (—OCO—R3), wherein R3 is a C1-C22 alkyl group or a C2-C22 alkenyl group,
wherein, if R2 is hydrogen R1 forms a group of above-shown formula,
wherein in compound 6, R is one of the following moieties:
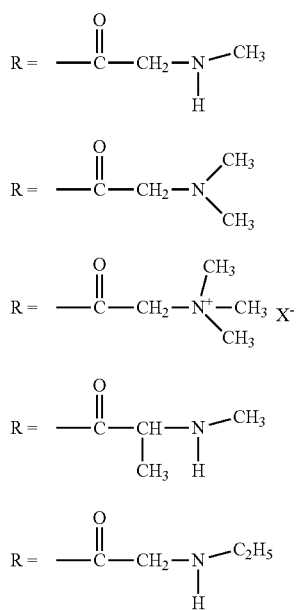
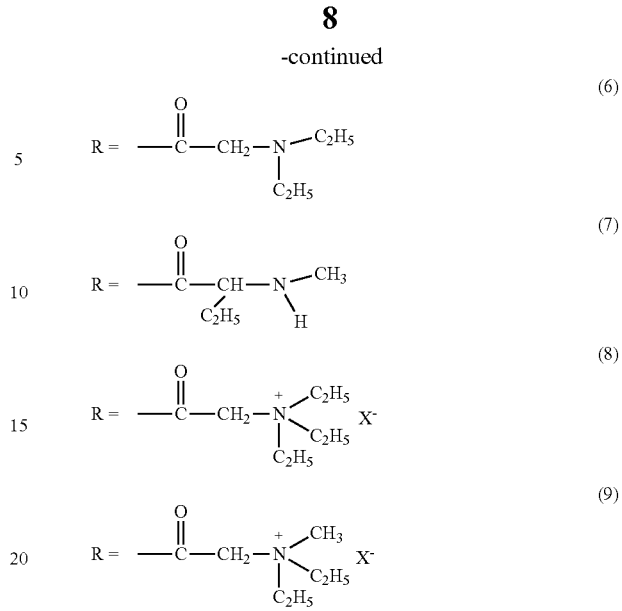
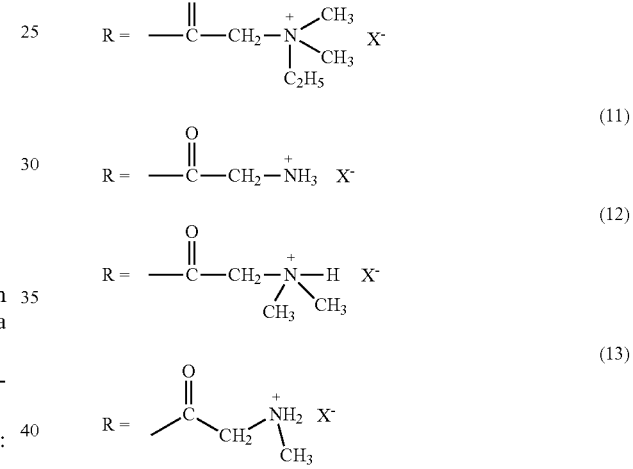
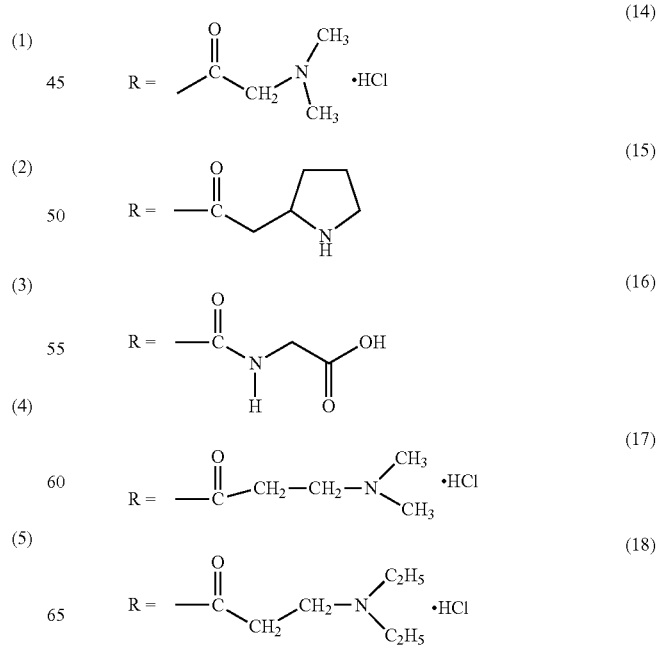

-continued

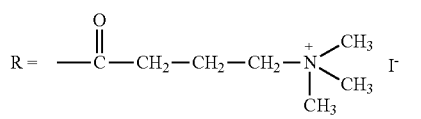

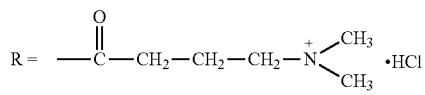

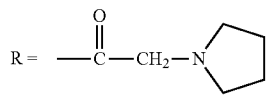

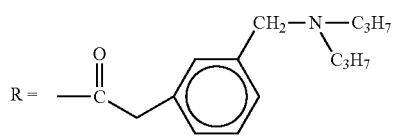

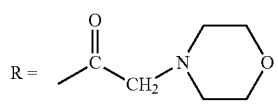

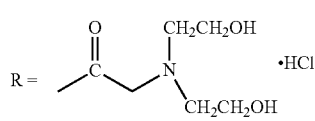

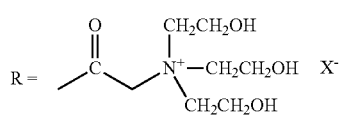

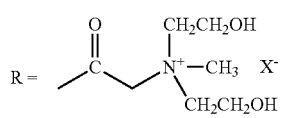

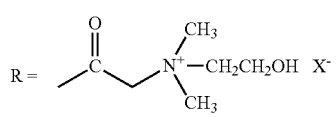

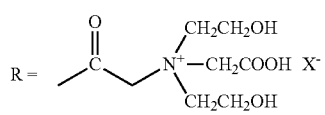

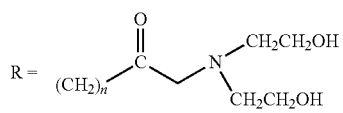

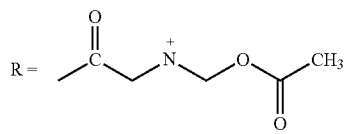

wherein X⁻ is a free soluble anion;
wherein in compound 8
R1=OCH3, R2=OH, R3=O-Glucose; or
R1=OCH3, R2=H, R3=O-Glucose; or
R1=OCH3, R2=OH, R3=OH; or
R1=OCH3, R2=H, R3=OH; or
R1=OH, R2=OH, R3=O-Glucose; or
R1=OH, R2=OH, R3=OH;
wherein in compound 12
R1, R2, R3, R4, R5, R6, R7, R8, R9, and R10 are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group; and provided that if compound 12 is monomeric, then compound 12 is other than resveratrol;
wherein in compound 15
R1, R2 and R3, independently from one another, represent H or (C1-C3)alkyl; R4 and R5 are identical or different and represent hydrogen, linear or branched (C1-C5)alkyl,
a prenyl group —CH2-CH═C(CH3)2,
a geranyl group —CH2-CH═C(CH3)(CH2)2CH═C(CH3)2
or R4 and R1, and independently R5 and R2, together with the atoms they are linked to, form one of the following groups:

with the provisos that R4 and R5 are not both hydrogen and that when R1=R2=R3=H, R4 and R5 are not a prenyl group and hydrogen, respectively,
wherein in compound 18 X, Y, and Z are either hydrogen or a protective group, provided that at least one of X, Y, and Z is the protective group.
A BCA may be a compound of formula 19:

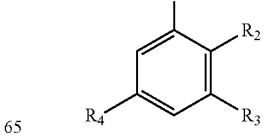

19 wherein in compound 19
R4 is selected from one of the following groups

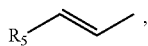, which is a suitable group to constitute a phenolic acid,

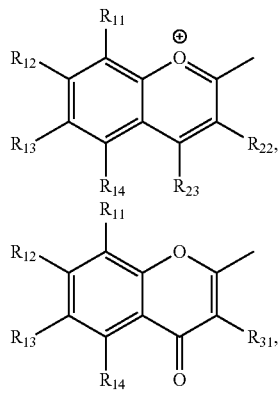

which are suitable groups to constitute a flavonoid,
or

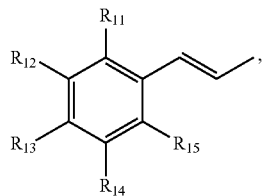, which is a suitable group to constitute a stilbenoid or a stilbenoid derivative,
wherein at least 2 of R1, R2, R3, R12, and R14 are —OH,
wherein R1, R2, R3, R5, R11, R12, R13, R14, R15, R21, R22 and R31 are independently from each other selected from
—H, —OH, —O—$R_{Alk}$, —CHO, —COR$_{Alk}$, —COOH, —COO—$R_{Alk}$, —CO—NH—$C_nH_{2n}$—COOH, —CO—NH—$C_nH_{2n}$—COO—,
—CN, —Cl, —Br, —I, —NO$_2$,
—$C_nH_{2n}$CN, —$C_nH_{2n}$—Cl, —$C_nH_{2n}$—Br, —$C_nH_{2n}$—I, —$C_nH_{2n}$—NO$_2$,
—O—PO$_3^{2-}$—O—PO$_3$H—, —O—PO$_3$H$_2$, —NH2, —NHR$_{Alk}$, —NR$_{Alk1}$R$_{Alk2}$, —N$^+$H$_3$, —N$^+$H$_2$R$_{Alk}$, —N$^+$HR$_{Alk1}$R$_{Alk2}$, —N$^+$R$_{Alk1}$R$_{Alk2}$R$_{Alk3}$,
—B(OH)$_2$, —OCHO, —O—COR$_{Alk}$, —OCF$_3$, —O—CN, —OCH$_2$CN,
wherein R$_{Alk}$, R$_{Alk1}$, R$_{Alk2}$, and R$_{Alk3}$ are alkyl residues which are independently selected from each other, preferably CH$_3$, C$_2$H$_5$, C$_3$H$_7$ or C$_4$H$_9$,
wherein in $C_nH_{2n}$ n is an integer, and $C_nH_{2n}$ preferably is CH$_2$, C$_2$H$_4$, C$_3$H$_6$, C$_4$H$_8$;
or wherein R1, R2, R3, R5, R11, R12, R13, R14, R15, R21, R22 and R31 are, independently from each other, one of the following moieties:

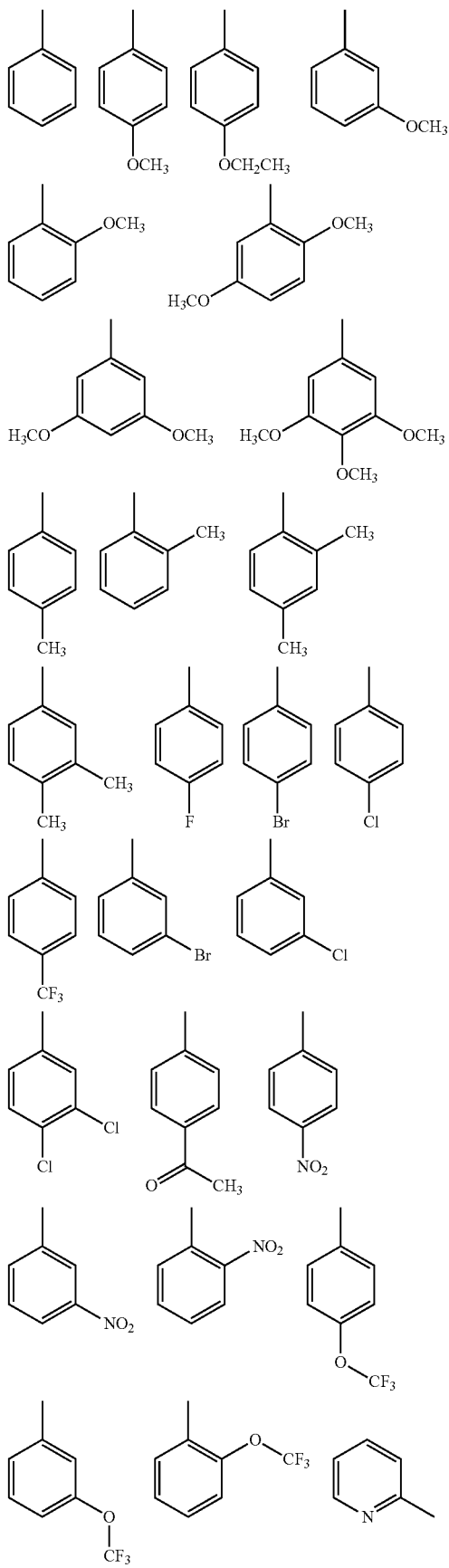

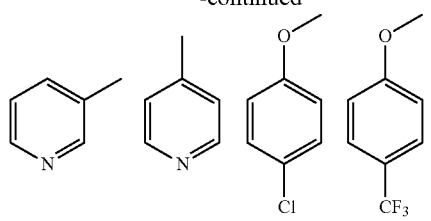
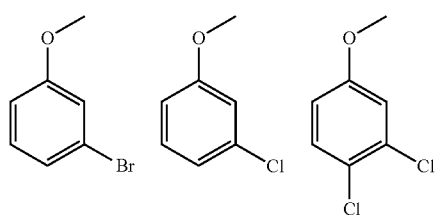
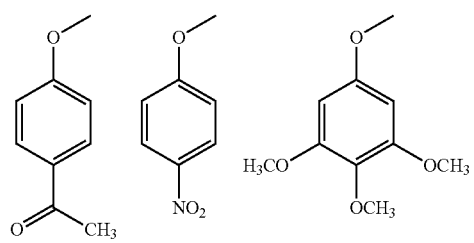
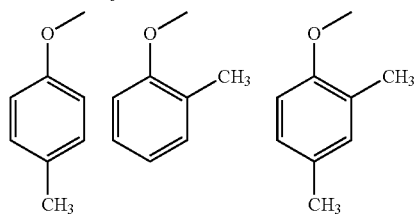
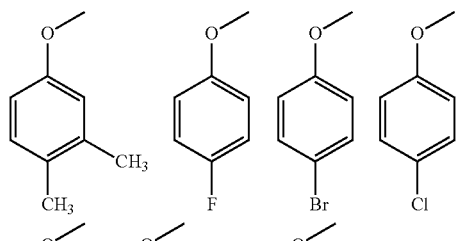
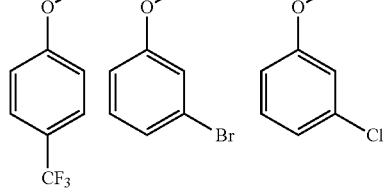
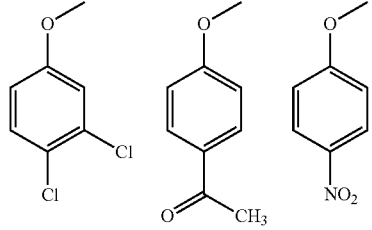
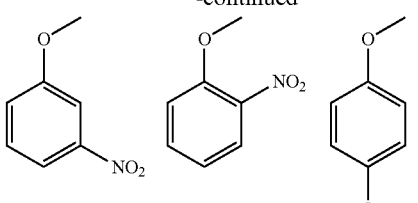
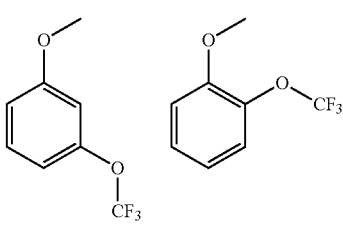
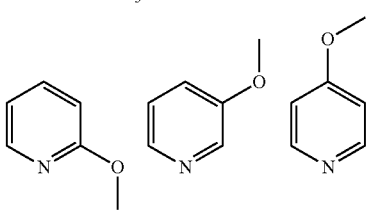
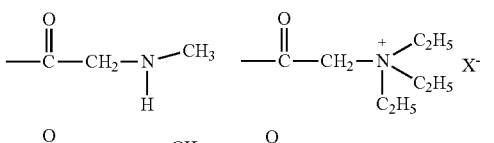
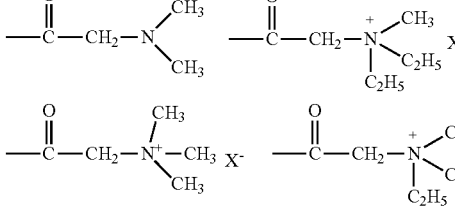
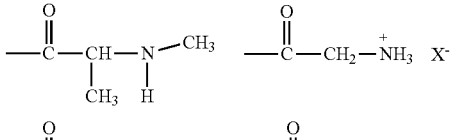
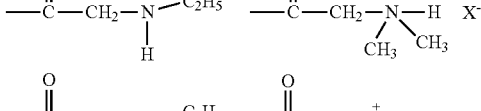
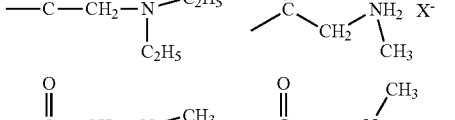
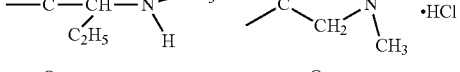
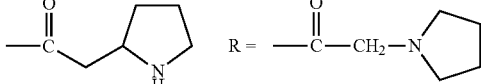
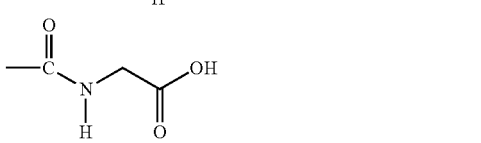

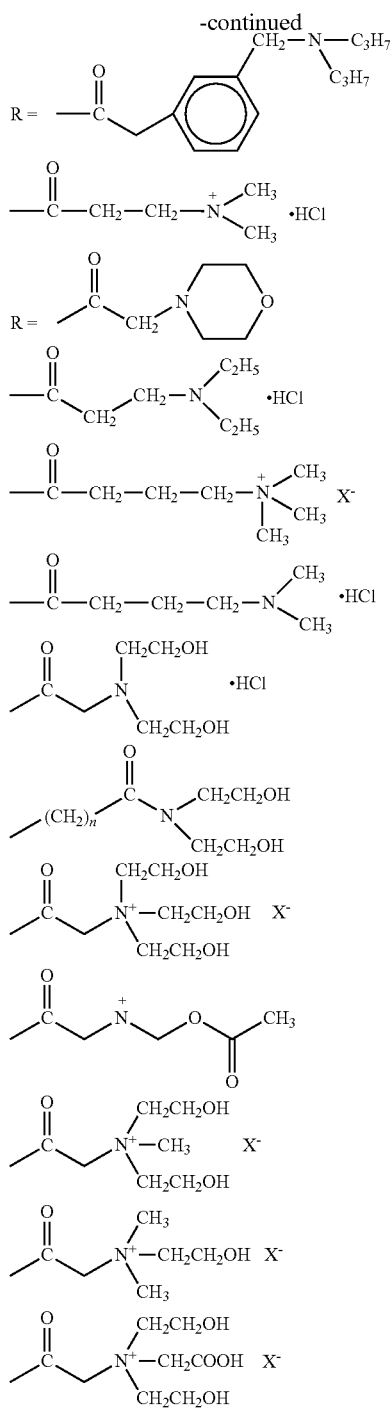

wherein X⁻ is a free soluble anion,
or wherein R11, R12, R13, R14 or R15 are a mono or oligo saccharide-residue, with the proviso that
at least 2 of R1, R2, R3, R11, R12, R13, R14 and R15 are independently selected from —OH, —O—R$_{Alk}$, —O—COR$_{Alk}$, —OCF$_3$, —O—CN, and —OCHO.

Alternatively, at least 2 of existing R1, R2, R3, R11, R12, R13, R14 may be —OH, to form a polyphenol.

Alternatively, at least one of existing R1, R2, R3, R11, R12, R13, R14 or R15 may be —OH to form a stilbenoid.

Alternatively, at least one of existing R1, R2, R3, R11, R12, R13, R14 or R15 may be —O—R41 to give non limiting examples of a stilbenoid derivative.

The BCA, preferably the polyphenolic compound, may be selected from the group comprising:

epsilon-viniferin, pallidol, trans-diptoindonesin B, hopeaphenol, oxyresveratrol, piceatannol, pterostilbene, or 4'-methoxy-(E)-resveratrol 3-O-rutinoside, phenolic acids such as gallic acid, ellagic acid, vanillic acid; propyl gallate, protocatechuic acid, p-coumaric acid, caffeic acid, danielone, syringic acid, salicylic acid, gentisic acid, p-hydroxy benzoic acid, rosmarinic acid, rosmanol, quinic acid, sinapic acid, epi-isorosmanol, isorosmanol, E-anethol, 3,4-dimethoxycinnamic acid, ferulic acid; phenolic diterpenes such as carnosol and carnosic acid; coumarines such as coumarin, ombelliferon, herniarine, esculedol, scopoletol, scopanone, fraxetol and their glucosides such as 7-O-glucosyl-ombelliferone, 6-O-glucosyl-esculetol, 7-O-glucosyl-esculetol, 7-O-Glucosyl-6-methoxycoumarine, dihydroxyisocoumarins such as 6-methoxymellein, as well as prenyloxycoumarines such as 7-geranyloxy coumarine, 7-methoxy-6-(3-methyl-2-butenyl)-coumarine, 7-methoxy-8-(3-methyl-2-butenyl)-coumarine; naphtoquinones such as 1,2-naphtoquinone, 1,4-Naphtoquinone, 2,6-Naphtoquinone, alkannin, hexahydroxy-1,4-naphthalenedione, juglone, lapachol, lawsone, menatetrenone, 2-methoxy-1,4-naphthoquinone, nigrosprin B, 2,3,5,7-tetrahydroxy-1,4-naphtalenedione, menadione, 5,8-Dihydroxy-1,4-naphtoquinone and other dihydroxynophtoquinones, atovaquone; flavonoids: anthoxanthins including flavonols such as quercetin, kaempferol, myricetin, fisetin, galangin, isorhamnetin, pachypodol, rhamnazin pyranoflavonols and furanoflavonols, flavones such as apigenin, luteolin and tangeritin, flavonoides including flavanones such as hesperetin and naringenin, eriodictoyl, homoeriodictoyl and sakuranetin, flavanonols such as taxifolin, dihydrolquercitin and dihydrokaempferol, flavans such as flavan-3ol (including Catechin, Gallocatechin, catechin 3'-gallate, gallocatechin 3-gallate, epicatechin, epigallocatechin, epicatechin 3-gallate, Epigallocatechin 3-gallate, theaflavin, theaflavin-3-gallate, theaflavin-3,3'-digallate, thearubigin, proaanthocyanidins, flavan-4-ol and flavan-3,4-diol; anthocyanins such as cyanidin, delphinidin, malvidin, pelargonidin, peonidin, petunidin, cyanin-3-rutinoside and delphinidin-3-rutinoside; isoflavonoides including isoflavones such as genistein, glycitein and daidzein, further including isoflavanes, isoflavenes, coumestans and pterocarpans stilbenoides including stilbene and aglycones such as piceatannol, pinosylvin, pterostilbene.

The BCA in the peritoneal therapeutic fluid may be solubilized by complexation to a cyclodextrin, or by conjugation to a soluble moiety, which means a water soluble moiety, or by contacting with nanoparticles, preferably water soluble nanoparticles.

The BCA in the peritoneal therapeutic fluid may be emulsified, for example by addition of a suitable surfactant.

The BCA in the peritoneal therapeutic fluid may be suspended, for example treatment of the compound of the PTF by ultrasound, thereby breaking larger particles of the compound into smaller particles.

The BCA in the peritoneal therapeutic fluid may be solubilized through chemical binding to a highly soluble moiety. Preferentially, the BCA in the peritoneal therapeutic fluid, if it is not PEG or a derivative of PEG, may be solubilized through pegylation with Polyethyleneglycol (PEG) or Methoxy-Polyethyleneglycol (mPEG).

As mentioned before, the BCA may be a polyethylene glycol (PEG), or a derivative of a polyethylene glycol, such as mPEG. So, a PEG or PEG derivative may be present in the PTF of the invention as a BCA on its own.

The following description relates to a) PEG or PEG derivative as an autonomous BCA and also to b) PEG or PEG derivative as a compound that is used for pegylation.

The PEG or mPEG may have a molecular weight above 400 Da.

The PEG or the mPEG may be selected from the group comprising PEG 600, mPEG 600, PEG 1000, mPEG 1000, PEG 1450, mPEG 1450, PEG 3350 and mPEG 3350, or the like.

In the Peritoneal therapeutic fluid, one or more BCAs may be present in a concentration of 0.001 mg/L to 5 g/L, preferentially between 0.001 mg and 1 g/l further preferred between 0.01 and 500 mg/L. These concentrations, and other concentrations for BCA that are given in g/L, relate to the total concentration of all BCA if more than one BCA is present.

In the Peritoneal therapeutic fluid, one or more BCAs may be present in a concentration of 0.05 to 60 µMol/L, preferentially between 0.05 to 40 µMol/L further preferred between 0.05 to 20 µMol/L. These concentrations, and other concentrations for BCA that are given in µMol/L, relate to the total concentration of all BCA if more than one BCA is present.

The term "between" is intended to include the lower and upper limit of the respective range, if not otherwise indicated. So, if a range is disclosed as "between X and Y", X and Y are included.

In the Peritoneal therapeutic fluid the one or more BCAs may be present in a concentration of 0.02 µM to 315 µM, preferentially 0.07 µM to 100 µM further preferred 0.2 µM to 50 µM. Said molar concentration relates to each individual BCA if more than one BCA is present.

The peritoneal therapeutic fluid may be used as a peritoneal dialysis fluid, as a peritoneal therapeutic fluid with decreased cytotoxicity on human peritoneal mesothelial cells. The peritoneal therapy fluids of the present invention are particularly suitable for use as peritoneal dialysis fluids.

The peritoneal therapeutic fluid may comprise one or more of an ingredient which is selected from the following: alkali metal ions,
alkaline earth metal ions, an osmotic agent, and/or a pH-buffer. In one embodiment, the peritoneal therapeutic fluid comprises an osmotic agent and/or a pH-buffer, and preferably also alkali metal ions and/or alkaline earth metal ions. An osmotic agent is an agent capable of increasing osmolality of a solution. An osmotic agent is preferably biocompatible.

The peritoneal therapeutic fluid may comprise at least one saccharide, which may be a mono-, oligo- or polysaccharide. Examples are fructose, glucose, maltose or maltodextrin.

The invention is also directed to a peritoneal therapeutic fluid container or kit comprising at least one liquid containing compartment, wherein liquid of at least one compartment contains a compound as mentioned above, wherein the compound is solubilized.

The Peritoneal therapeutic fluid container or kit may comprise at least two compartments, which after mixation generates a peritoneal therapeutic fluid as defined above, wherein at least one compartment contains a solubilized BCA as mentioned above.

The Peritoneal therapeutic fluid container or kit may comprise at least two compartments, which after mixation generate a peritoneal therapeutic fluid as defined above, wherein at least one compartment contains a dry and unsolubelized BCA (for example in powder form) as mentioned above, that maybe solubilized by contacting liquid from one of the other compartments, just before application.

The peritoneal dialysis fluid container or kit may comprise one or several compartments, wherein at least one compartment contains a part of a dialysis fluid comprising an osmotic driver such as glucose, maltodextrin or other sugars or sugar polymers, aminoacids, cyclodextrins, Polyethylene glycols (PEGs) or other osmotic drivers, or derivatives of such osmotic drivers or a mixture of the described osmotic driver compounds and/or their derivatives.

The peritoneal dialysis fluid container or kit may comprise one or several compartments, wherein at least one compartment contains a BCA as described before in dry or solubilized form, for example as a part of a dialysis fluid comprising the BCA in a solubilized formulation.

The Peritoneal therapeutic fluid container or kit may be used in peritoneal dialysis.

A BCA, in the present application, is preferably a polyphenolic compound or derivative thereof that presents a PDF induced cyto-toxicity decreasing activity. BCAs also include metabolized derivates of polyphenolic compounds that exhibit cyto-toxicity decreasing activity in presence of fluids for peritoneal treatment.

DETAILED DESCRIPTION OF THE INVENTION

Further embodiments of the present invention are provided hereunder.

The term polyphenolic compound comprises compounds that are characterized by at least two phenolic hydroxyl groups. In other words, a polyphenol comprises at least two hydroxyl groups which are bound to one or more aromatic rings.

The term "glycoside of a polyphenolic compound" is used in the present application to refer to a polyphenolic compound to which a sugar moiety is bound via a glycosidic bond. The sugar moiety is preferably bound to a hydroxyl group of the polyphenolic compound via a glycosidic bond, thereby forming an acetal of the sugar moiety. The sugar moiety may be a monosaccharide, a disaccharide, a trisaccharide, or an oligosaccharide. In a glycoside of a polyphenolic compound, one or more sugar moieties may be bound to a polyphenolic compound, respectively, preferably via one or more hydroxyl groups.

The term "bio-compatibility enhancing agents" ("BCA") is particularly used in the present application to refer to a polyphenolic compound, a metabolite of a polyphenolic compound which is obtained by metabolization in the human or animal body, a salt of a polyphenolic compound, a glycoside of a polyphenolic compound, derivatives of such compounds, or a polyphenolic compound that is chemically linked to a solubilizing moiety, such as a pegylated polyphenolic compound. So, in the present invention the aforementioned compound are also designated as BCAs. Preferred BCAs are stilbenoids and derivatives thereof, even more preferred resveratrol and derivatives thereof, such as piceid (polydatin), piceid glucosides, Piceatannol, and Pterostilbene.

BCAs in the present application may include, and may be characterized as, cyto-toxicity reducing agents. Polyphenols and derivatives thereof, preferred stilbenoids and derivatives thereof, even more preferred resveratrol and derivatives thereof, such as piceid, piceid glucosides, Piceatannol, and Pterostilbene; or solubilized polyphenols and derivatives thereof, which may be modified by complexation to solubilizing agents such as cyclodextrins, or modified through conjugation to highly soluble molecules, preferentially conjugated to a Polyethylene glycol (PEG), are further included in the scope of BCAs as defined in the present specification.

A stated above, also polyethylene glycol (PEG), or a derivative of a polyethylene glycol, such as mPEG can be a BCA on its own.

The PEG that is used for binding to another BCA may be activated. Activation preferably means that PEG comprises a functional group that allows coupling to another compound. Examples are given below.

In the present specification, the terms "polyethylene glycol 600", "polyethylene glycol 1000", "polyethylene glycol 1450", "polyethylene glycol 3350" refer to linear polyethylene glycols that are generally known and commercially available for example as Carbowax PEGs.

In order to link the PEGs to a polyphenol, preferentially a stilbenoid, more preferentially resveratrol, a piceid or a piceid glucoside, PEGs have to be covalently bound to the BCAs, a process known as pegylation. To allow pegylation, PEG has to be activated.

For example "activated PEGs" can be coupled to polyphenolic Compounds, as a means of attaching bound biocompatibility enhancing additive to fixed supports or to solubilize them in aqueous fluids. Commercially available examples for "activated PEGs" are:
Methoxy PEG Hydrazide: CH3O—(CH2CH2O)n-CH2-CO—NH—NH2,
Methoxy PEG Amine HCl Salt: CH3O—(CH2CH2O)n-CH2-CH2-NH2HCl,
Methoxy PEG Propionaldehyde: CH3O—(CH2CH2O)n-CH2-CH2-CHO,
Methoxy PEG Thiols: CH3O—(CH2CH2O)n-CH2-CH2-SH,
Methoxy PEG Vinylsulfone: $CH_3O$—$(CH_2CH_2O)$n-$CH_2$—$CH_2$—$SO_2$—$CH=CH_2$,
Methoxy PEG Maleimide,
Methoxy PEG Nitrophenyl Carbonate: CH3O—(CH2CH2O)n-CO—O—C6H4-NO2,
Methoxy PEG Succinimidyl Carbonate,
Methoxy PEG Succinimidyl Carboxymethyl Ester,
Methoxy PEG Succinimidyl Carboxyl Ester,
Methoxy PEG Succinimidyl Carboxypentyl Ester,
Aminoalkyl PEGs: CH3O—(CH2CH2O)n-(CH2)n'-NH2.

The terms "peritoneal therapy fluid" (PTF) is used in the present application to refer to a fluid that can be used in a peritoneal therapy. Peritoneal therapies encompass, for example, peritoneal nutrition, peritoneal dialysis, peritoneal detoxification in case of liver failure or drug abuse, treatment of primary and secondary peritoneal cancer, treatment of peritoneal infections and peritonitis, pre- or post-operative peritoneal treatment, or peritoneal administration of systemic treatments. A "peritoneal dialysis fluid" (PDF) is a "peritoneal therapy fluid" (PTF) that is used for peritoneal dialysis.

Peritoneal therapy is carried out by applying a peritoneal therapeutic fluid to the peritoneum. As an active ingredient, a Peritoneal therapeutic fluid of the invention may comprise a polyphenolic compound, a metabolite of a polyphenolic compound which is obtained by metabolization in the human or animal body, or a glycoside of a polyphenolic compound, or a derivative of these compounds. Further possible ingredients are disclosed in this description.

The terms "peritoneal therapy fluid" (PTF), and "peritoneal dialysis fluid" (PDF) are particularly used in the present application to refer to an aqueous solution comprising physiological amounts of various electrolytes in concentrations comparable to those in the blood.

The peritoneal therapy fluid (PTF) may comprise one or more of the following components:
sodium, preferably in an amount of (about) 90 to (about) 150 mEq/L;
potassium, preferably in an amount of (about) 0 to about 5 mEq/L;
calcium, preferably in an amount of (about) 0 to (about) 6 mEq/L;
magnesium, preferably in an amount of (about) 0 to (about) 4 mEq/L;
alkali equivalent, such as lactate, acetate, citrate, bicarbonate or phosphate, preferably in an amount of (about) 25 to (about) 50 mEq/L; Alkali equivalents may also be called pH buffers. The PTF of the invention may contain lactate at a concentration between 10 and 100 mM and/or bicarbonate at a concentration between 5 and 100 mM, or other physiologically acceptable pH buffers.
an "osmotic agent", such as glucose and maltodextrin or other mono- and/or polymeric sugar molecules, aminoacids, cyclodextrins, PEGs, or other biocompatible compounds, that may be administered at concentrations sufficient to increase osmolality, derivatives of such compounds and mixtures of such compounds and/or their derivatives, preferably at a total concentration between 0.5 and 20% (by weight). Commonly applied osmotic agents are salts, glucose, dextrose or oligosaccharides obtained from limited hydrolysis of polysaccharides and derivatives thereof, preferably at concentrations between 0.5 and 20%. Other osmotic agents may be glucose polymers, aminoacid mono- or multimers, cyclodextrins, PEGs or proteins, or compositions thereof.

A "peritoneal therapeutic fluid" (PTF) or a "peritoneal dialysis fluid" (PDF) is introduced and maintained in the peritoneal cavity of a patient in need of such treatment or of dialysis, for a time period of usually 1 to 24 hours. After treatment has occurred, the fluid is removed from the patient's peritoneal cavity.

Peritoneal therapeutic fluids preferably contain one or a mixture of several "osmotic agents", to establish physiological osmolality. In case of Peritoneal dialysis fluids, in many cases osmolality is higher than physiological osmolality in order to draw liquid and small molecular weight "waste molecules" out of the patient's blood into the dialysate. PDFs are usually applied at osmolalities between about 280 and 500 mOsm/kg.

In a further embodiment, a peritoneal therapeutic fluid of the invention comprises one or more of a saccharide, wherein the saccharide may be a monosaccharide, a disaccharide, an oligosaccharide or a polysaccharide, or any mixture thereof, preferably a mono- or oligo-saccharide, which is an ingredient of the PTF. In the present invention it was found that solubility and stability of a polyphenolic compound, of a metabolite of a polyphenolic compound, of a salt or of a derivative of a polyphenolic compound such as a glycoside of a polyphenolic compound, or of derivative of these compounds, can be increased when a peritoneal therapy fluid comprises one or a mixture of mono- and/or oligo-saccharides. Preferred saccharides are selected from biologically metabolizable or biologically inactive saccharides such as fructose, glucose, sucrose, maltose or dextrins. Further embodiment related to saccharides are described in the following paragraphs.

The saccharide preferably has a maximum molecular weight of 50 kD. 1 D (Dalton) corresponds to 1 g/mol. More preferably, the molecular weight is in a range of 90 D-50 kD.

Said molecular weight is range of a molecular weight of molecules present in the saccharide. The saccharide can be a mixture of saccharides of different chain lengths (different numbers of monosaccharide units). So, the saccharide preferably has a molecular weight distribution in the range of 90 D-50 kD.

The molecular weight of oligo/poly-saccharides may vary widely:

In one embodiment, the at least one saccharide has a molecular weight of 90 D to 500 D. (1 D=1 g/mol).

In one embodiment, the at least one saccharide has a molecular weight of 90 D to 1.5 kD.

In one embodiment, the at least one saccharide has a molecular weight of 1.5 kD to 50 kD.

In another embodiment, the at least one saccharide has a molecular weight of 350 D to 50 kD.

As mentioned, the saccharide may be a monosaccharide, a disaccharide, an oligosaccharide or a polysaccharide, wherein an oligo- or polysaccharide, or a mixture of different mono-, di-, oligo- and/or poly-saccharides. A polysaccharide preferably comprises, or is composed of, up to 500 monosaccharide units in maximum.

A mono-saccharide may be selected from a triose such as glyceraldehyde and glucerone, a tetrose, such as erythroses, threose and erythrulose, a pentose, such as ribose, arabinose, xylose, lyxose, ribulose and xylulose, or a hexose, such as allose, altrose, glucose, mannose, gulose, idose, galactose, talose, psicose, fructose, sorbose and tagatose, and may also be defined as a saccharide of a molecular weight of roughly 90 to 200 D.

The term saccharide may be selected from derivatives of mono-saccharide, such as aminoglycosides, such as glucosamine, galactosamine, N-acetylglucosamine, N-acetylgalactosamine, which may not or may be sulfated to different degrees.

A mono-saccharide may be further selected from uronic sugars, such as glucuronic acid or iduronic acid.

A di-saccharide may be selected from sucrose, Gentiobiulose, Laminaribiose, Gentiobiose, Rutinulose, Xylobiose, trehalose, β,β-Trehalose, α,β-Trehalose, lactulose, sophorose, lactose, cellobiose, chitobiose, or from reducing alpha-disaccharides such as maltose, Kojibiose, Nigerose, Isomaltose, Turanose, Maltulose, Palatinose (Isomaltulose), Mannobiose, Melibiose, Melibiulose, Rutinose, and may also be defined as a saccharide of a molecular weight of about 150 to 400 D.

The term di-saccharide may further comprise glycosaminoglycan-di-saccharides", preferably glucosaminoglucan-di-saccharides, composed of an aminoglucoside and a monosaccharide, which may be acetylated or sulfated to different degrees.

An oligo-saccharide may be Trisaccharides or saccharides of higher degree of polymerization, selected from an oligomer of above cited saccharides, a product of limited hydrolysis of a linear or branched homo-polysaccharide, such as a amylose, amylopectin, fructan such as inulin, glucan, galactan and mannan, cellulose, arabic gum, amylose, amylopectin, glycogen, dextran, and hemicellulose, a product of limited hydrolysis of a hetero-polysaccharide, such as hemi-cellulose, arabinoxylose, or pectine, or a product of limited hydrolysis of a mixed polysaccharide, such as starch.

In a more specific embodiment a oligo-saccharide may be an alpha-glucan, preferably a reducing alpha glucan, with a degree of polymerization of 3 or higher, exemplified by, but not limited to isomaltotriose, nigerotriose, maltotriose, melezitose; maltotriulose, raffinose, kestose, maltodextrins of different molecular weight or other hydrolysis products from alpha glucans, such as Dextran, glycogen, pullulan, floridean starch, starches, amylose, amylopectine, hydrolyzed starches, and mixtures thereof, preferably with molecular weights between 300 D and 300 KD.

The term "saccharide" also comprises derivatives of a saccharide. So, the saccharide may be a derivative of a saccharide, such as an oxidized saccharide, such as a saccharic acid, or another acidic saccharide, such as a sulfuric ester groups containing saccharide, a deoxy-saccharide, an acetylated saccharide or an amylated saccharide, and corresponding homo- and hetero-oligo-saccharides.

The term saccharide may further comprise oligo- and/or poly-saccharides composed of composed of "glycosaminoglycan-disaccharides", also called Glycosaminoglycans or mucopolysaccharides.

In a specific embodiment, alpha-Glucosaminoglycans, such as Heparins, are selected.

In one embodiment, the saccharide is selected from glucose, fructose, sucrose, maltose, a homo-oligomer thereof, a hetero-oligomer thereof, or a mixture thereof.

In another embodiment the saccharide is selected from glucose, icodextrin, or a mixture thereof.

In another embodiment the saccharide is selected from a reducing alpha-glucan, and/or a reducing derivated alpha-glucan, exemplified but not limited to a heparin or a heparin derivate, and one or several saccharide mono- and di-mers.

In the frame of this application oligo-saccharides and polysaccharides cover saccharides composed of between 3 and 500 monosaccharide-units, preferably 3 to 300 monosaccharide-units. In another definition, oligo-saccharides and polysaccharides have to a molecular weight between 250 D and 50 KD. Preferably, an oligosaccharide means saccharides composed of between 3 to 20 monosaccharide-units. Preferably, a polysaccharide means saccharides composed of between 21 to 500 monosaccharide-units.

Icodextrin, which is a type of maltodextrin or can be derived from maltodextrin, is a polydisperse mixture of polymers with varying chain lengths (2-300 linked glucose molecules corresponding to a molecular weight of 350 to 50 kD), its molecular weight is characterized by both a number average (Mn) and a weight average (Mw) molecular weight. The number average molecular weight Mn for icodextrin, ranges from 5000 to 6500 Da and the weight average molecular weight Mw ranges from 13 000 to 19000 Da (Garcia-Lopez et al., Peritoneal Dialysis International, Vol. 29, p 370).

As for oligo-saccharides, MW of polysaccharides is very heterogeneous. For example, the Mw (Berry method) of starch from waxy corn is $2.27 \times 10^8$ Da, waxy rice $8.9 \times 10^7$ Da, cassava $5.7 \times 10^7$ Da, Hylon V $2.7 \times 10^7$ Da, Hylon VII $4.8 \times 10^6$ Da, and potato amylose $1.9 \times 10^5$ Da (Yokoyama et al., Cereal chemistry, volume: 75, 530.

In certain applications, such as "power-drinks" artificial poly-saccharides of a size of up to 700 KD are advertised.

The at least one saccharide may be present in a total concentration of ≥0.02% by weight (200 mg/L). It has been shown that a concentration as low as this concentration enhances polyphenol stability.

The at least one saccharide may be present in a total concentration of ≥0.75% by weight (7.5 g/L). It has been shown that such concentration enhances polyphenol stability and/or solubility of polyphenol.

The at least one saccharide may be present in a total concentration of ≥2.4% by weight. It has been shown that such concentration further enhances polyphenol stability and/or solubility of polyphenol.

The at least one saccharide may be present in a total concentration of ≥5% by weight. It has been shown that such concentration further enhances polyphenol stability and/or solubility of polyphenol.

The at least one saccharide may be present in a total concentration of ≥7.5% by weight (75 g/L). It has been shown that such concentration enhances polyphenol stability and solubility of polyphenol.

The at least one saccharide may be present in a total concentration of ≥20% by weight (200 g/L). It has been shown that such concentration further enhances polyphenol stability and solubility of polyphenol.

The upper limit of concentration of the at least one saccharide is preferably the concentration of saturation. Another possible upper limits, that could be combined with any of the lower limits in this description, are 45%, 40%, 30% by weight.

In a more specific embodiment, the at least one saccharide of a molecular weight of 90 D to 500 D and is present in a total concentration of ≥0.02% (200 mg/L) minimum, thereby enhancing polyphenols solubility and/or stability.

In a more specific embodiment, the at least one saccharide of a molecular weight of 90 D to 500 D is present in a total concentration of ≥0.75% (7.5 g/L) minimum, thereby enhancing polyphenols solubility and/or stability.

In a further specific embodiment, the at least one saccharide of a molecular weight of 90 D to 500 D is present in a total concentration of ≥7.5% (75 g/L) minimum, thereby enhancing polyphenols solubility and stability.

In a more specific embodiment the at least one saccharide of a molecular weight of 350 D to 50 kD is present in a total concentration of ≥0.02% by weight (200 mg/L), thereby minimum enhancing polyphenol solubility and/or stability.

In a further specific embodiment, at least one saccharide of a molecular weight of 350 D to 50 kD is present in a total concentration of ≥0.2% by weight (2 g/L), thereby enhancing polyphenol solubility and/or stability.

In a further specific embodiment, at least one saccharide of a molecular weight of 350 D to 50 kD is present in a total concentration of ≥2% by weight (20 g/L), thereby enhancing polyphenol solubility and/or stability.

In a further specific embodiment, at least one saccharide of a molecular weight of 350 D to 50 kD is present in a total concentration of ≥5% by weight (50 g/L), thereby enhancing polyphenol solubility and/or stability.

In a further specific embodiment, at least one saccharide of a molecular weight of 350 kD to 50 kD is present in a total concentration of ≥7.5% by weight (75 g/L), thereby enhancing polyphenol solubility and/or stability.

Different concentrations of the at least one saccharide may be employed. If more than one saccharide, i.e. more than one type of saccharide, is present, the concentration refers to the total concentration of all saccharides present in the solution.

If in this description concentrations are given in percent by weight, 1% by weight corresponds to 10 g/L.

A concentration of said mono- or oligo-saccharide of 0.02% (200 mg/L) significantly increases polyphenol stability. A concentration of ≥0.75%, preferably ≥7.5%, further preferably ≥20% of saccharides, preferably of molecular weight of 50 D to 1.5 kD, enhances polyphenol stability and solubility. A concentration of ≥0.02% (200 mg/L), preferably ≥0.75% (7.5 g/L), more preferably ≥2.4% (24 g/L), further preferably ≥5% (50 g/L) enhances polyphenol solubility and stability.

The concentration ranges for saccharide can be combined with any concentration ranges described herein for a BCA.

A sugar can also fulfill the function of an osmotic agent, as described herein. The sugar is not covalently bound to the BCA, i.e. the cytotoxicity reducing agent. The sugar is preferably a dissolved component of a PTF.

Solubility of Polyphenolic BCAs may also be increased by amino acids, and therefore such BCAs may also be applied to amino acid containing peritoneal therapeutic or dialysis solutions. The Peritoneal therapeutic fluid may therefore comprise at least one amino acid. One or more amino acids may be present individually or as mixtures at concentrations between 0.01 and 10% for therapeutic liquids, or at higher concentrations, if highly concentrated BCA shall be formulated.

The present invention provides and claims peritoneal therapy fluids (PTFs) comprising bio-compatibility enhancing additives (BCAs), as addressed in the definitions.

Bio-compatibility enhancing additives are preferably used at concentrations between 0.001 mg/L and 5 g/L in the dialysis fluid, a concentration of 0.001 mg/L to 1 g/L is further preferred, a concentration of 0.01 to 500 mg/L is especially preferred.

Concentrations of BCA in the present invention are preferably measured after 1 hour stirring at room temperature (which is preferably 20-23° C., more preferably 22° C.), particularly if the BCA is a polyphenolic compound, a metabolite of a polyphenolic compound which is obtained by metabolization in the human or animal body, a salt of a polyphenolic compound, a glycoside of a polyphenolic compound, or derivative of these compounds. So, concentrations of said compound correspond to measured solubility after 1 hour stirring at room temperature. Concentration is measured in a PTF of the invention. So, BCA can be dissolved in water. Other ingredients of a PTF, which are mentioned in this description, are preferably present. If not specifically indicated, or if not specifically indicated otherwise, the time of stirring is one hour. In some cases, other stirring times are indicated, such as 12 hours. The fact that solubility after one hour stirring cannot be equated with a maximum or absolute concentration is illustrated by the fact that for example the concentration of resveratrol after 1 hour stirring between 10 and 15 mg/L evolves above 24 mg/L after 12 hours.

Bio-compatibility enhancing agents may be polyphenols, preferentially stilbenoids, such as resveratrol; or derivatives thereof, preferentially glucoside-stilbenoids such as piceid or piceid glucosides, Piceatannol, or Pterostilbene; or solubilized Polyphenols through complexation, such as cyclodextrin-polyphenol complexes or through conjugation with a highly soluble moiety such as PEG, resulting in pegylated polyphenols, preferentially pegylated stilbenoids, more preferentially pegylated resveratrol, piceid, piceid glucoside, Piceatannol, and Pterostilbene.

In another embodiment, the invention provides PTFs comprising any combination of above described BCAs.

In another embodiment of the present invention, it is preferred that the PTF is a peritoneal dialysis fluid.

In another embodiment of the present invention, one BCA, or multiple BCAs in combination, are present in a concentration of 0.001 mg/L to 5 g/L. The present inventor has surprisingly found that these BCAs or BCA combinations reduce cyto-toxicity of commonly applied peritoneal dialysis fluids, thereby increasing biocompatibility of PTFs.

In a preferable embodiment of the invention, one BCA, or multiple BCAs in combination, are present in a concentration of 0.001 to 1 g/L.

The present inventor has surprisingly found that these BCAs or BCA combinations reduce cyto-toxicity of commonly applied peritoneal dialysis fluids, thereby increasing biocompatibility of PTFs.

In a further preferable embodiment of the invention, one BCA, or multiple BCAs in combination, are present in a concentration of 0.01 to 500 mg/L.

The present inventor has surprisingly found that these BCAs or BCA combinations reduce cyto-toxicity of commonly applied peritoneal dialysis fluids, thereby increasing biocompatibility of PTFs.

In another aspect, the invention provides a process for manufacturing of a PTF herein described, using methods known to the one of ordinary skill in the art.

In a further aspect, the invention provides with a peritoneal therapeutic fluid container or kit comprising at least one liquid containing compartment, wherein liquid of at least one compartment contains a BCA as mentioned before, wherein the BCA is solubilized. The liquid containing compartment may comprise a saccharide as disclosed before, wherein the saccharide is preferably selected from glucose, an alpha-glucan, glucose di- tri- or oligo-mers, maltodextrin, icodextrin, or alpha-glucan polysaccharide hydrolysate of higher average molecular weight, or a mixture thereof. In this aspect, the peritoneal dialysis container or kit may contain a BCA solubilized in the PTF, or in one of the fluids composing the final PTF.

In a further aspect, the invention provides with a Peritoneal therapeutic fluid container or kit comprising at least two compartments, also called multicompartment container, wherein at least one compartment contains a BCA as mentioned before, wherein the BCA may be in solid form or in liquid solution, solubilized or in suspension. At least one compartment may comprise a solubilized BCA in concentrated form.

A multicompartment container preferably comprises at least one dry compartment, containing one or several BCAs in solid form, preferably powder form, to be solubilized just before application of the PD solution. At least one further compartment may comprise a liquid. A solid BCA in a first compartment maybe solubilized by contacting with a liquid from one of the other compartments, just before application. A liquid from one of the other compartments may comprise a saccharide as disclosed before, wherein the saccharide is preferably selected from glucose, maltodextrin, icodextrin, or a mixture thereof, or one of the other saccharides as mentioned before.

In a further aspect, a PTF container or kit is described, comprising one or multiple compartments, wherein at least one compartment contains a part of a dialysis fluid comprising glucose, maltodextrin, aminoacids PEGs, cylcodextrins or alternative osmotic drivers, or a derivative of such osmotic drivers, or a mixture of any such molecules, in a dialysis fluid as described above.

In yet another aspect, a multi-compartment container or kit may contain at least one compartment containing a sugar or sugar polymer derived osmotic agent under acidic conditions (pH between 1 and 6). The container or kit may further be characterized in that at least one second compartment contains a further part of the dialysis fluid at basic pH, which, upon mixture with the fluid from the first compartment, reconstitutes a PTF with a pH between 6.5 to 8, preferably between 6.8 and 7.5.

Molecular weight in the present invention is preferably measured by gel permeation chromatography (GPC), preferably gel permeation chromatography with light scattering and refractive index detection (GPC-RI-MALLS). A number of polysaccharide units, which corresponds to a degree of polymerization, can be determined with these methods. A more detailed, but non-limiting, method is given in the examples.

Figure 1:
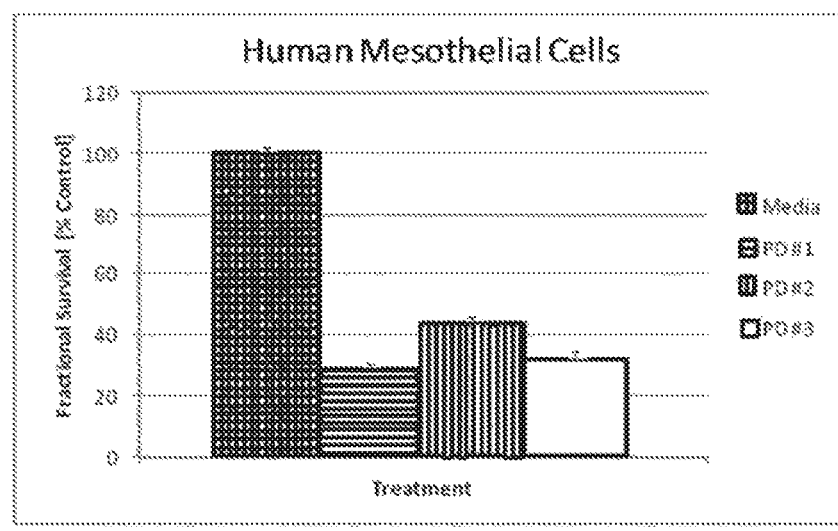
FIG. 1 Comparative testing of PDFs after 48 hours results in decreased resazurin to reorufin conversion.

The following Examples illustrate embodiments of the present invention:

EXAMPLES

Molecular Weight Measurement:

The saccharides are dissolved in extra-pure water in a concentration of 0.5% (w/v). The solutions are heated at 95° C. for 30 minutes. The polymers are analyzed using the following devices: Alliance chromatography system (Waters corporation, Milford, Mass., USA), DAWN-EOS light scattering detector (Wyatt Technology, Santa Barbara, USA) with $\lambda_0=658$ nm and 16 detectors in the range of angles from 14.4 to 163.3°, K5 flow cell. The polymers are fractionated on a precolumn and three columns having the separation ranges 300-$10^4$, $5\times10^4$-$2\times10^6$ and $10^6$-$10^8$ (SUPREMA-Gel, PSS Polymer Standards Service GmbH, Mainz, Germany). 100 µl of solution are injected. The fractionation takes place at a temperature of 30° C. and a flow rate of 0.8 ml/min with 0.05M NaNO3 as eluent. The Astra V 5.1.8.0 program (from Wyatt Technology, Santa Barbara, USA) is used to analyze the molecular weight distribution of the samples. Same procedure can be used when molecular weight of other compounds than saccharides are measured.

Dialysis Solutions:

In accordance with this invention, peritoneal dialysis fluids are provided, containing an osmolality sufficient to cause diffusion of water and waste products across the peritoneum after infusion of the peritoneal dialysis fluid into the peritoneal cavity of a patient. In addition to an osmotic agent or a combination of osmotic agents, the present peritoneal dialysis fluid contains amounts of various physiologically important electrolytes in concentrations comparable to those in plasma. A suitable peritoneal dialysis fluid has been described in the definitions part of this patent.

TABLE I

| PD Sol Osmolality (mOsm/kg) | PD#1 StaySafe ® 346 | PD#2 Physioneal ® 485 | PD#3 Extraneal ® 284 | PD#4 StaySafe ® 486 |
|---|---|---|---|---|
| Osmotic Agent | Glu | Glu | Ico | Glu |
| (%) w/v | 1.25 | 3.86 | 7.5 | 4.25 |
| Sodium (mEq/L) | 132 | 132 | 133 | 132 |
| Calcium (mEq/L) | 3.5 | 1.75 | 3.5 | 3.5 |
| Magnesium | 0.5 | 0.25 | 0.5 | 0.5 |
| Chloride | 96 | 101 | 96 | 96 |
| Lactate | 40 | 10 | 40 | 40 |
| Bicarbonate |  | 25 |  |  |
|  | pH 5.5 | pH 7 | ph 5.5 | pH 5.5 |
| tested BCA | /, R, P, PE | /, R, P, PE | /, R, P, PE Pa, Pt, CA, Lu, De | /, P, Pa, Pt, CA, Lu, De |

Legend to Table I:
Solutions tested for their application as peritoneal dialysis fluids. Abbreviations: Glu, glucose; Ico, icodextrin; OsAg, osmotic agent; BCA, added "biocompatibility enhancing agent". Concentrations in % (w/v) and mEq/L; osmolality in mOsm/kg. Tested BCAs are: The stilbenoids Resveratrol (R), Piceid (Polydatin) (P), Piceatannol (Pa), Pterostilbene (Pt); the phenolic acid Cafeic Acid (CA), the flavonoides Luteolin (Lu), Quercetin (Qu), Delphinidin (De). PEG 1450 Carbowax (PE).
Legend to Table I:
Solutions tested for their application as peritoneal dialysis fluids. Abbreviations: Glu, glucose; Ico, icodextrin; OsAg, osmotic agent; BCA, added "biocompatibility enhancing agent". Concentrations in % (w/v) and mEq/L; osmolality in mOsm/kg. Tested BCAs are: R Resveratrol, P Piceidand PE PEG 1450 Carbowax.

Table 1 shows peritoneal dialysis fluids, compared for testing the effect of reduction of cytotoxicity by addition of tested BCAs. The study involves evaluation of additions of BCAs at different concentrations to PD solutions.

StaySafe 1.25 solution was chosen to show impact of acidic pH at low Glucose concentration in an environment of high lactate buffer. Physioneal 3.86 was chosen to show the impact of high glucose concentration at physiological pH in an environment of low lactate buffer. StaySafe 4.25 was chosen to show combined challenge of acidic pH and high glucose concentration. Extraneal was chosen to compare the difference of glucose and maltodextrin at acidic pH and at high lactate concentration.

The examples show that addition of specifically selected BCAs increase biocompatibility of currently marketed PDFs. Those skilled in the art readily understand that addition of such "biocompatibility enhancing agents" will increase long term biocompatibility of any peritoneal therapeutic and/or dialysis solution, more specifically of such solutions containing sugar and/or sugar polymer-derived osmotic agents or such, and this even in cases and models where certain dialysis solutions do not show immediate cytotoxicity and/or very low AGE formation.

Solutions are applied to different toxicity experiments in absence or presence of specifically selected BCAs, to show that BCAs, exemplifying the present invention, decrease cytotoxic side-effects, and thereby increasing biocompatibility, as compared to reference solutions without such BCAs.
Toxicity:

The following experiments compare the cytotoxicity of reference solutions in absence or presence of BCAs of this invention, to show increased biocompatibility of dialysis solutions in presence of BCAs of this invention.

Examples 1, 2, 3, and 4

Experimental comparison of different dialysis solution with respect to their effect on human peritoneal mesothelial cells, applying the following protocol.

Cell Culture
Experimental Procedure:

Human peritoneal mesothelial cells (HPMC) were purchased from Zen Bio Inc. and cultured in cell culture flasks using suppliers media. Near confluent HPMC were harvested by trypsinization, seeded into collagen-coated 96-well tissue culture plates (Corning) and allowed to adhere overnight. The medium was changed to twice diluted with dialysis solution for 48 up to 72 hours.

Cell viability was established applying the promega resazurin assay, following the suppliers protocol. Living cells are metabolically active and are able to reduce the non-fluorescent dye resazurin to the strongly-fluorescent dye resorufin. The fluorescence output is proportional to the number of viable cells over a wide concentration range. This also allows the calculation of the proliferation rate for cells capable of consecutive cell division. Resazurin is effectively reduced in mitochondria making it also useful to assess mitochondrial metabolic activity. For the dose-response relationship, relative viability was plotted against the test item concentrations.

In the case of Piceid, the intra-cellular ATP level was determined with the CTG assay. For this, media was completely removed from all wells by aspiration, 60 µl of CTG reagent was added to each well, and incubated for 5 min at RT while softly shaking (50 rpm). Using a Victor3 1420 Multilabel Counter, the emitted luminescence produced in the CTG assay was measured. For the dose-response relationship, absolute luminescence (background subtracted) was related to the negative (medium) control and relative viability values were plotted against the test item concentrations. For the dose-response relationship, absolute luminescence (background subtracted) was related to the negative (medium) control and relative viability values in presence of BCA were plotted against the BCA concentrations.

All assays were conducted in a duplex format using the same cell culture.
Results:

Example 1

Comparative testing of PDFs after 48 hours results in decreased resazurin to reorufin conversion, which translates to decreased cell-viability. See FIG. 1.

Example 2

Addition of selected BCAs of this invention partially reestablished reszurin to reorufin conversion, which is interpreted as a result of a decreased cytotoxicity, due to the application of the tested BCAs. Compounds were added at 9 dilutions (Cmax=500 µM) together with tested PD solutions or Medium control. Incubation was 48 hours.

Figure 2:
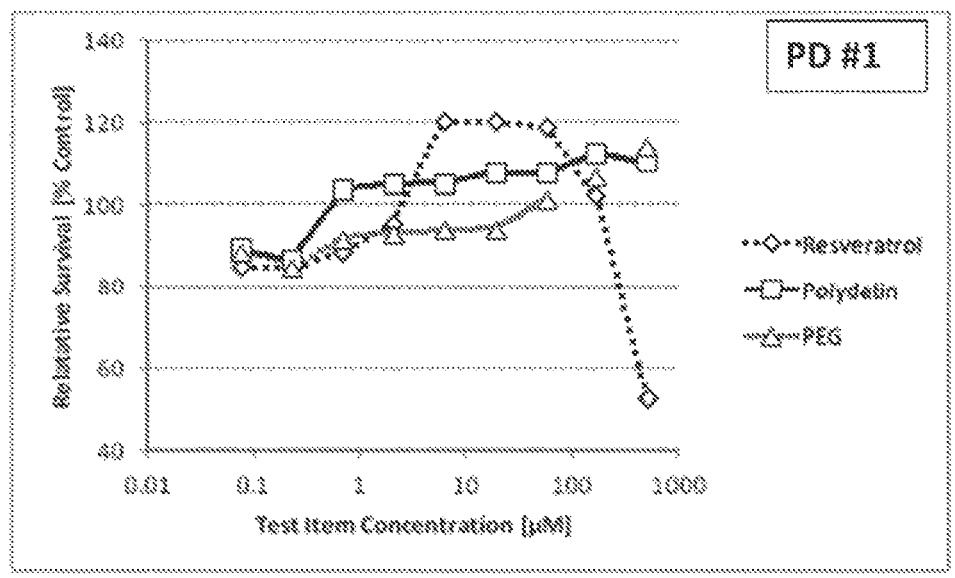
FIG. 2 Results of resazurin to reorufin conversion, Resveratrol, Polydatin, PEG, PD solution #1.
Figure 3:
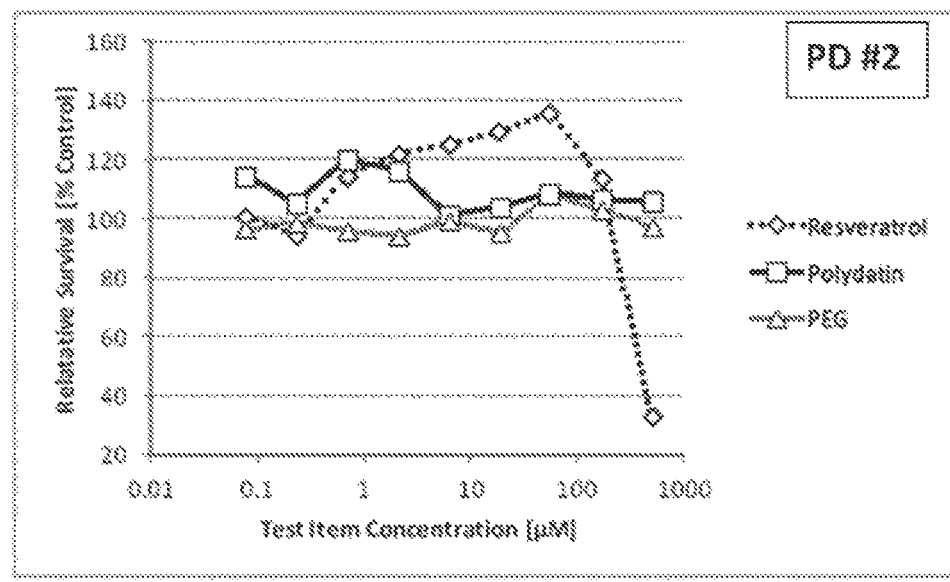
FIG. 3 Results of resazurin to reorufin conversion, Resveratrol, Polydatin, PEG, PD solution #2.
Figure 4:
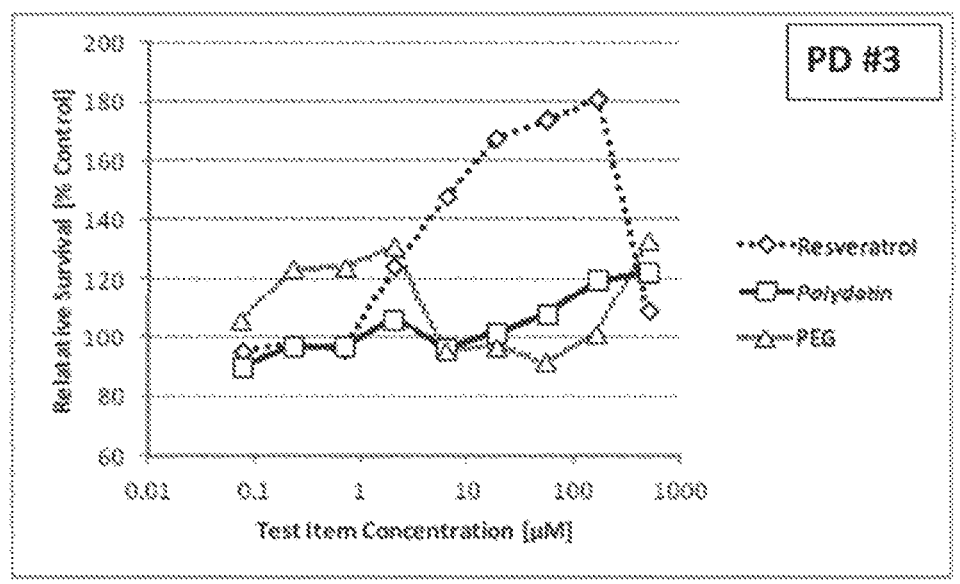
FIG. 4 Results of resazurin to reorufin conversion, Resveratrol, Polydatin, PEG, PD solution #3.
Figure 5:
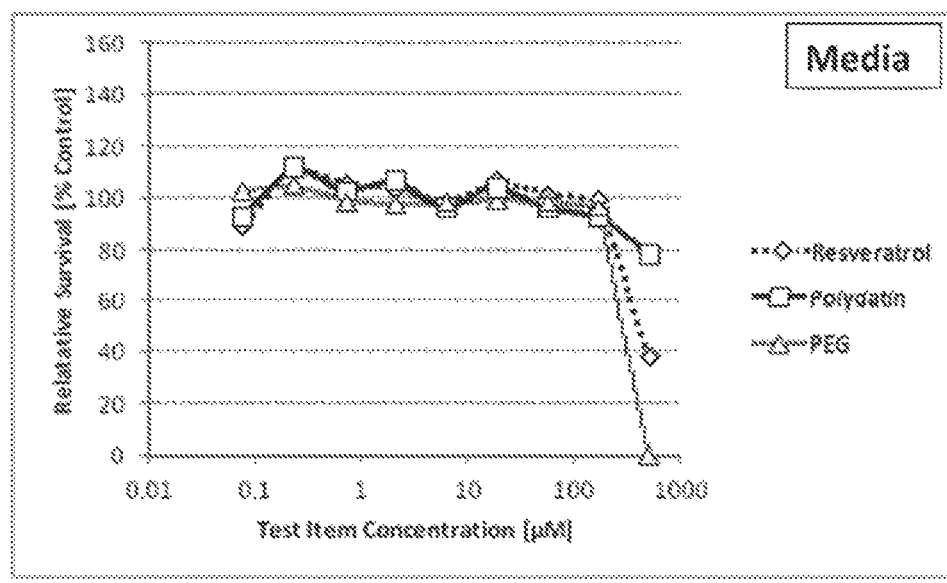
FIG. 5 Results with Medium control.

Results with PD-Solution #1 are presented in FIG. 2
Resveratrol improves cell viability of HPMC cells up to 20%. Piceid (polydatin) shows minor improvements.
Results with PD-Solution #2 are presented in FIG. 3.
Resveratrol improves cell viability of HPMC cells up to 40%. Piceid (polydatin) shows minor improvements.
Results with PD-Solution #3 are presented in FIG. 4.
Resveratrol improves cell viability of HPMC cells up to 40%. PEG shows minor improvements.
Medium Control is presented in FIG. 5:
In control medium, without cytotoxic stress, resveratrol, piceid (polydatin) and PEG have no significant effect on cell viability until Cmax.

In conclusion, we obtained a strong effect of Resveratrol reducing cyto-toxicity of all three tested peritoneal dialysis solutions and a minor effect of piceid. A possible explanation for a relatively weaker effect of piceid is, that piceid has first to be converted to resveratrol or another biological active compound by enzymes that are present in the peritoneum. We therefore shall show a stronger effect of piceid in an animal model.

For PD-solution #3 we observed a cytotoxicity decreasing effect of PEG. We had used PEG simply as a control in our experiments and have no explanation for this observation.

Example 3

Figure 6:
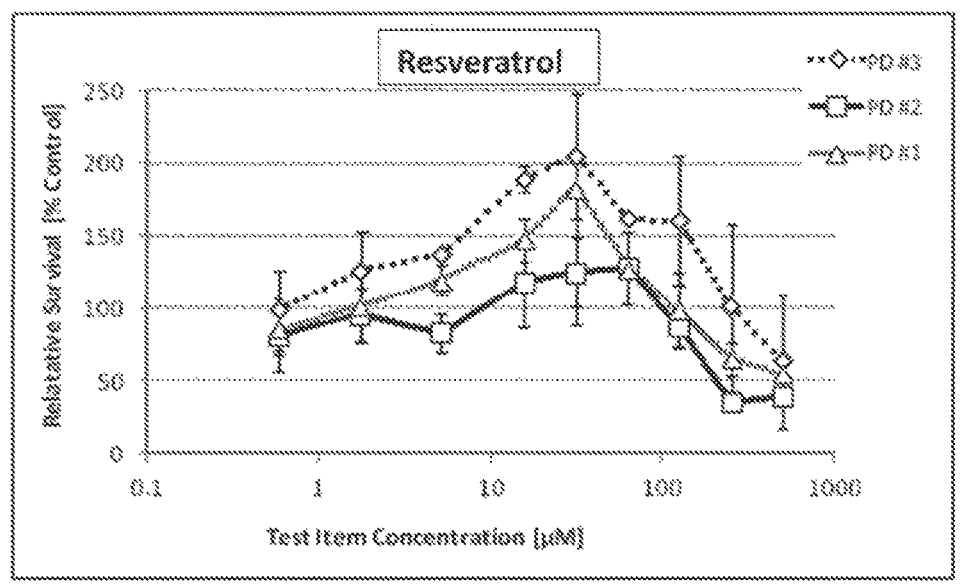
FIG. 6 Results of resazurin to reorufin conversion, Resveratrol in different PD solutions.

Addition of selected BCA resveratrol partially reestablished resazurin to reorufin conversion, in a triplicate assay, which is interpreted as a result of a decreased cytotoxicity, due to the application of the tested BCA. In this series, Resveratrol was added 5 minutes in advance to application of test-solutions, at 9 dilutions (Cmax=500 µM). Incubation was 72 hours. Results are presented in FIG. 6.

Resveratrol improves viability of HPMC cells exposed to PD-Solution #1 by up to 84%.

Resveratrol improves viability of HPMC sells exposed to PD-Solution #2 by up to 28%.

Resveratrol improves viability of HPMC cells exposed to PD-Solution #3 by up to 105%.

Example 4

Addition of selected BCAs, namely of
the stilbenoids Piceatannol (Pa), Pterostilbene (Pt), Piceid (Polydatin) (P);
the phenolic acid Cafeic Acid (CA);
the flavanoides Luteolin (Lu), Delphinidin (De);
partially reestablished resazurin to reorufin conversion, or partly re-established intracellular ATP-level, which is interpreted as a result of a decreased cytotoxicity, due to the application of the tested BCA. Test items were tested at 3 replicates per concentration. All assays were conducted in a duplex format using the same cell culture. Incubation was 72 hours.

Figure 7:
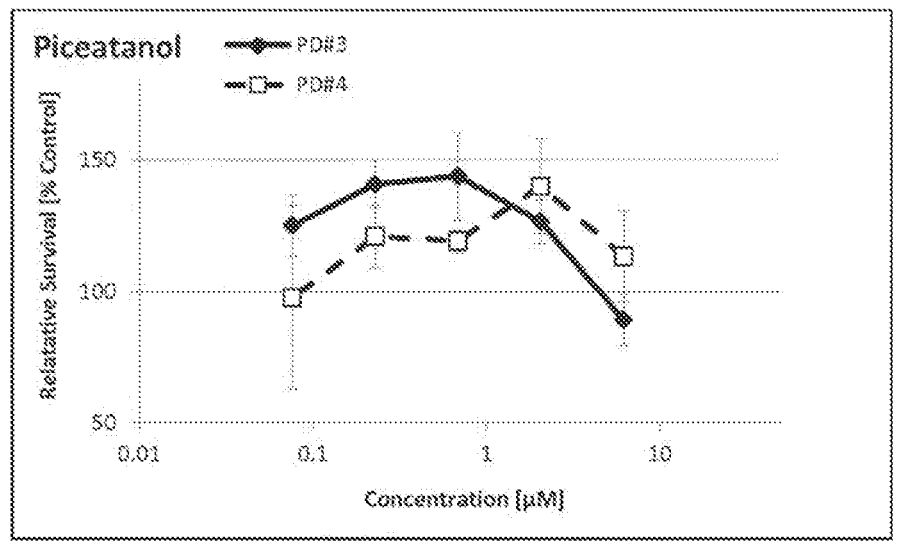
FIG. 7 Results of resazurin to reorufin conversion, Piceatannol in different PD solutions.

Results with Piceatannol are presented in FIG. 7
Piceatannol improves cell viability of HPMC cells, when exposed to PD-Solution #3 by up to 44%, and when exposed to PD-Solution #4 by up to 40%.

Figure 8:
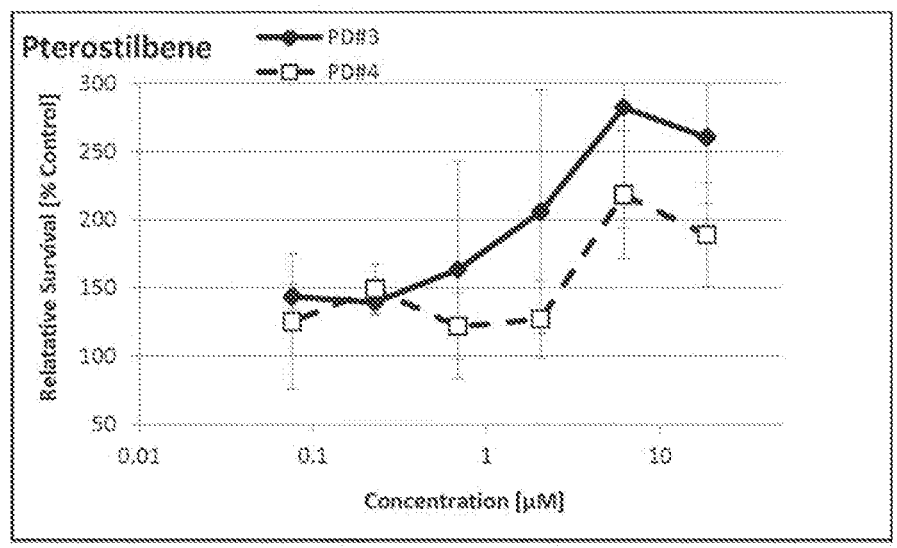
FIG. 8 Results of resazurin to reorufin conversion, Pterostilbene in different PD solutions.

Results with Pterostilbene are presented in FIG. 8
Pterostilbene improves cell viability of HPMC cells, when exposed to PD-Solution #3 by 183%, and when exposed to PD-Solution #4 by 118%.

Figure 9A:
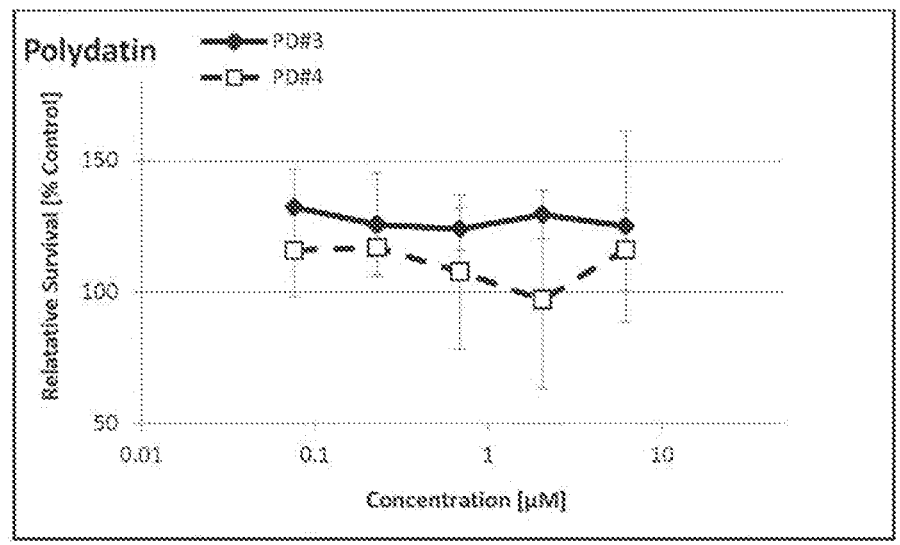
FIG. 9A, 9B Results of resazurin to reorufin conversion, Piceid in different PD solutions.
Figure 9B:
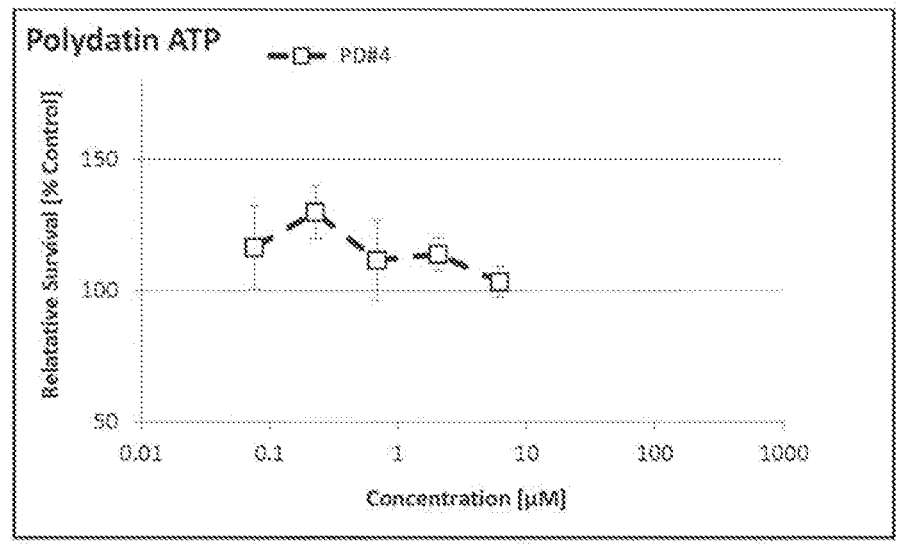

Results with Piceid (Polydatin) are presented in FIGS. 9a. and b. In this experimental series, Piceid improved viability of HPMC cells measured by resazurin to resorufin transformation, when exposed to Solution #3 by up to 32%, when exposed to PD-Solution #4 by up to 17% (FIG. 9a). Measured by ATP-level re-establishment, Piceid improves viability of HPMC cells exposed to PD-Solution #4 by 51%.

Figure 10:
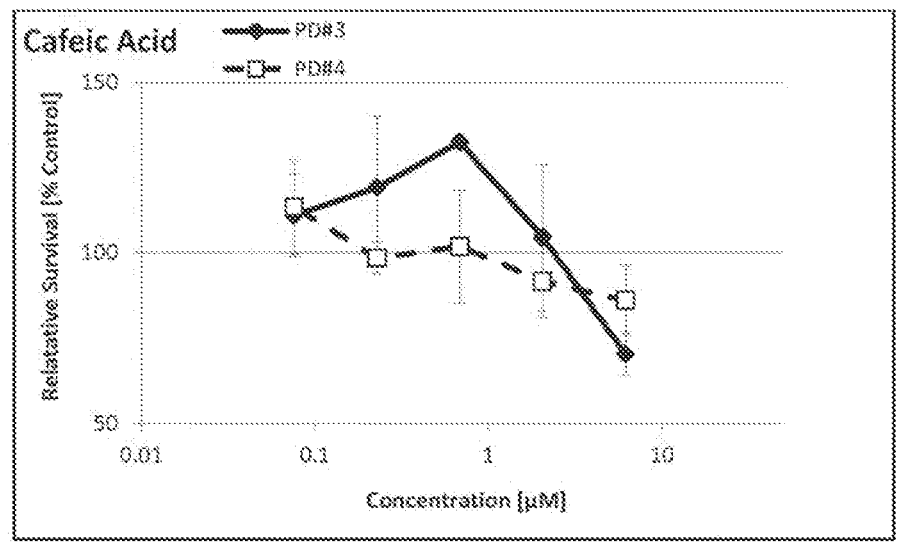
FIG. 10 Results of resazurin to reorufin conversion, Caffeic acid in different PD solutions.

Results with Cafeic Acid are presented in FIG. 10.
Cafeic Acid improves cell viability of HPMC cells, when exposed to PD-Solution #3, up to 32%. Cell viability improvement is minor when HPMC cells are exposed to PD-Solution #4.

Figure 11:
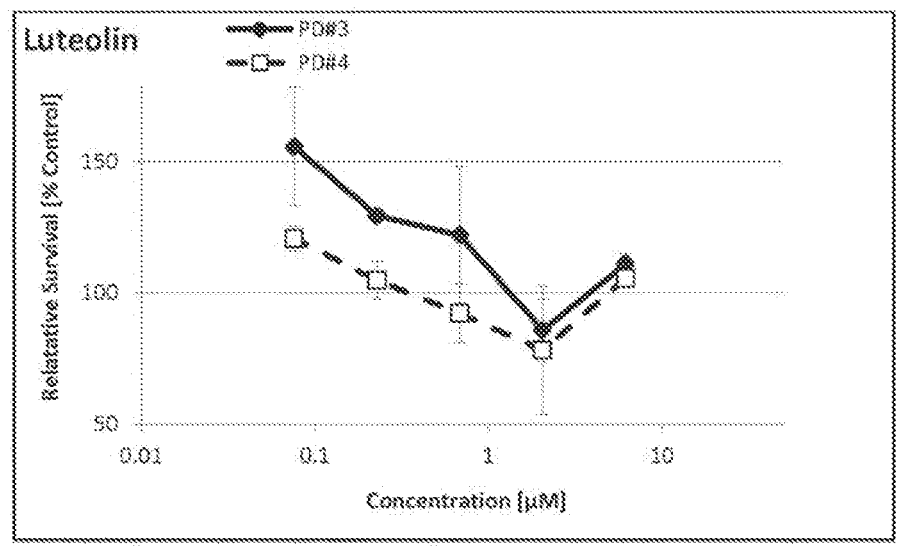
FIG. 11 Results of resazurin to reorufin conversion, Luteolin in different PD solutions.

Results with Luteolin are presented in FIG. 11.
Luteolin improves cell viability of HPMC cells, when exposed to PD-Solution #3 by up to 56%, and when exposed to PD-Solution #4 by up to 21%.

Figure 12:
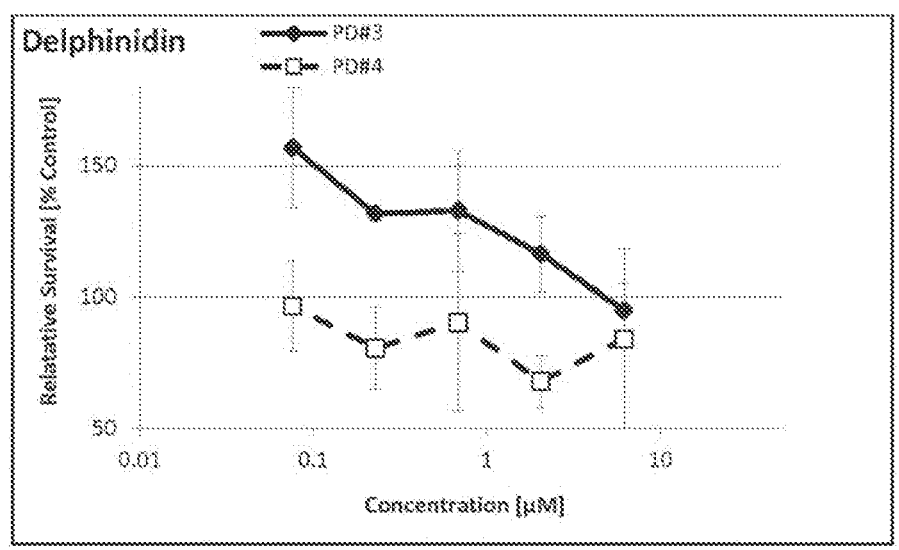
FIG. 12 Results of resazurin to reorufin conversion, Delphinidin in different PD solutions.

Results with Delphinidin are represented in FIG. 12.

Delphinidin improves cell viability of HPMC cells, when exposed to PD-Solution #3 by up to 57%. No cell viability improvement du to Delphinidin was observed under the applied experimental conditions, when testing HPMC cells expose to PD-Solution #4.

Taken together, results from examples 1 to 4 indicate a general effect of tested BCAs by increasing cell-viability of HPMC cells, when exposed to PD-Solutions. For most BCAs the concentration of maximal activity varies between 0.08 µM and 18.5 µM, but in some cases concentrations of 167 or even 500 µM were highly efficacious. For those skilled in the art such variability of concentration with highest efficacy is not surprising, reflecting different bio-availbilities and target affinities. Nevertheless, such a general impact of so many representatives of given classes of naturally occurring compounds within the same model is a striking discovery.

All tested compounds (Polyphenols) showed some improvement of HPMCs when exposed to at least one of the 4 tested PD-Solutions. All tested Stilbenoids (Resveratrol, Piceid, Piceatanol and Pterostlben) increased cell viability as well on Glucose based as ond Icodextrin based PD-Solutions.

The phenolic acid Cafeic Acid, and flavanoides Luteolin and Delphinidin mainly improved Icodextrin based dialysis solutions.

Those, skilled in the art understand that a toxicity cell model is a relatively fragile model, and that measurable cell-culture toxicity decrease is already dependent on measurable cell-toxicity in the first place. Nevertheless we observed overall higher stress due to Icodextrin based PTFs as compared to Glucose Based PTFs, under the applied experimental conditions. Such stronger toxicity challenge enabled us to show BCA activity of tested compounds over a larger range of concentrations. The results of Piceid show highest variation of all tested compounds. We believe that the need of metabolization of piceid, dependent on metabolic capacity of cultured cells, might be a reason for such variability. In example 4 we succeeded to show reproducible BCA activity of Piceid in 3 different experimental set-ups.

Example 5

Figure 13:
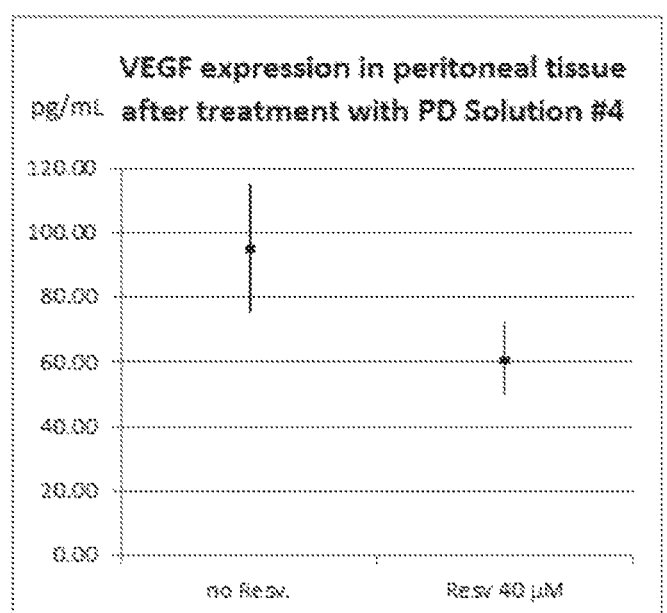
FIG. 13 Results of peritoneal VEGF expression in Sprague-Dawley rats after 2 to 4 weeks Peritoneal Dialysis with PD solution #4 in absence or presence of Resveratrol 40 µM (average concentrations and standard deviations).

Animal Studies have been carried out as described in Lee et al. 2012:
Experimental Procedure:

Peritoneal access ports were inserted in male Sprague-Dawley rats. After one week, rats started to received peritoneal treatment: 10 rats receive once daily 20 ml of Sol #4, 10 rats received 20 ml of Sol #4 with addition of selected BCA (resveratrol), during 2 hour infusions. After 2 to 4 weeks, the abdomen was opened, the peritoneum was recovered and submitted to protein extraction. Tissue VEGF concentration was established by ELISA (Abcam Rat VEGF ELISA Kit, ab100787) on obtained protein preparations (pg/ml).
Results:

Increased VEGF expression after chronic peritoneal dialysis has been reported in humans and rat-models, and is related to fibrosis and angiogenesis as side effects of long term peritoneal dialysis treatment (Zweers, 2001; Park, 2004). Results of example 5 (table II and FIG. 13) show that addition of selected BCA (resveratrol) decreases expression of VEGF in the peritoneum of standard PDF treated rats, indicating improved biocompatibility of BCA supplemented PDFs in the animal model.

TABLE II

VEGF expression in peritoneal tissue after 2 or 4 weeks of peritoneal dialysis wit Solution #4 in absence or presence of Resveratrol 40 μM. Values between 2 and 4 weeks were highly reproducible and therefore combined for the statistical analysis.

| PD Solution | Treatment (weeks) | Animal | VEGF concentration (pg/mL) in prot. prep. | Statistical results |
|---|---|---|---|---|
| Sol #4 | 2 | 1 | 81.64 | Average |
|  |  | 2 | 80.21 | 95.18 |
|  |  | 3 | 93.52 | Stand. Dev. |
|  |  | 4 | 92.56 | 20.08 |
|  |  | 5 | 84.42 |  |
|  | 4 | 6 | 84.42 |  |
|  |  | 7 | 136.91 |  |
|  |  | 8 | 95.72 |  |
|  |  | 9 | 77.05 |  |
|  |  | 10 | 125.32 |  |
| Sol #4 + 40 μM Resveratrol | 2 | 11 | 50.21 | Average |
|  |  | 12 | 39.99 | 60.94 |
|  |  | 13 | 70.88 | Stand. Dev. |
|  |  | 14 | 77.84 | 10.65 |
|  |  | 15 | 60.12 |  |
|  | 4 | 16 | 62.02 |  |
|  |  | 17 | 63.71 |  |
|  |  | 18 | 57.91 |  |
|  |  | 19 | 68.45 |  |
|  |  | 20 | 58.23 |  |
| t-test pval |  |  |  | 0.00065 |

REFERENCES

Barre, Chen, Cooker, Moberly. Adv Perit Dial. 1999; 15:12-6.

Catalan, Reyero, Egido, Ortiz. J Am Soc Nephrol. 2001; 12(11):2442-9.

Ha, Yu, Choi, Cha, Kang, Kim, Lee. Perit Dial Int. 2000; 20 Suppl 5:S10-18.

Konings, Schalkwijk, van der Sande, Leunissen, Kooman. Perit Dial Int. 2005; 25(6):591-5.

Lee, Kang, Kim, Nam, Paeng, Kim, Li, Park, Kim, Han, Yoo, Kang, 2012, Laboratory Investigation 92: 1698-1711.

Mangram, Archibald, Hupert, Tokars, Silver, Brennan, Arduino, Peterson, Parks, Raymond, McCullough, Jones, Wasserstein, Kobrin, Jarvis. Kidney International, Vol. 54 (1998), pp. 1367-1371

Park, Lee, Kim, Kim, Cho, Kim. Perit Dial Int. 2004; 24(2):115-22.

Moriishi, Kawanishi. Perit Dial Int. 2008; 28 Suppl 3:S96-S100.

ter Wee, Ittersum. Nat Clin Pract Nephrol. 2007; 3(11):604-12.

Williams, Craig, Topley, Von Ruhland, Fallen, Newman, Mackenzie, Williams. J Am Soc Nephrol 2002; 13:470-479.

Zweers, Struijk, Smit, Krediet. 2001. J Lab Clin Med. 137(2):125-32.

The invention claimed is:

1. A method comprising administering to a human patient a peritoneal therapeutic fluid, the peritoneal therapeutic fluid comprising at least one biocompatibility enhancing agent (BCA), wherein the BCA is resveratrol, dihydro-resveratrol, piceid, piceatannol, pterostilbene, piceid glucoside, caffeic acid, luteolin, or a salt thereof, to conduct peritoneal dialysis on the human patient, wherein cytotoxicity on human peritoneal mesothelial cells is decreased compared to other peritoneal therapeutic fluids that do not contain the BCA, wherein the at least one BCA is present in a concentration of between 0.05 to 20 μMol/L, and wherein the peritoneal therapeutic fluid comprises electrolytes.

2. The method according to claim 1, wherein the peritoneal therapeutic fluid is an aqueous solution comprising:
sodium in an amount of 90 to 150 mEq/L;
potassium in an amount of 0 to 5 mEq/L;
calcium in an amount of 0 to 6 mEq/L;
magnesium in an amount of 0 to 4 mEq/L; and
an alkali equivalent in an amount of 25 to 50 mEq/L.

3. The method according to claim 1, wherein the peritoneal therapeutic fluid further comprises at least one saccharide.

4. The method according to claim 1, further comprising at least one disaccharide selected from the group consisting of sucrose, Gentiobiulose, Laminaribiose, Gentiobiose, Rutinulose, Xylobiose, trehalose, β,β-Trehalose, α,β-Trehalose, lactulose, sophorose, lactose, cellobiose, chitobiose, maltose, Kojibiose, Nigerose, Isomaltose, Turanose, Maltulose, Palatinose, Mannobiose, Melibiose, Melibiulose, and Rutinose.

5. The method according to claim 1, wherein the peritoneal therapeutic fluid further comprises maltodextrin or at least one oligosaccharide that is a product of limited hydrolysis of one of more of the following: starch, amylose, amylopectin, fructan, glucan, galactan, mannan, cellulose, arabic gum, glycogen, dextran, hemicellulose, arabinoxylose, and pectin, wherein the product of limited hydrolysis has a molecular weight of 90 D to 500 kD.

6. The method according to claim 1, wherein the peritoneal therapeutic fluid further comprises at least one alpha-glucan with a degree of polymerization of 3 or higher and has a molecular weight of 90 D to 500 kD.

7. The method according to claim 1, wherein the peritoneal therapeutic fluid further comprises at least one saccharide which is selected from the group consisting of isomaltotriose, nigerotriose, maltotriose, melezitose, maltotriulose, raffinose, kestose, maltodextrin, dextrins, heparin, Dextran, glycogen, pullulan, starch, amylose, amylopectin, icodextrin, and combinations thereof.

8. The method according to claim 1, wherein the peritoneal therapeutic fluid further comprises at least one saccharide which has a molecular weight in a range of 90D to 50 kD, 90D to 500 D, 90D to 1.5 kD, 1.5 kD to 50 kD, 350D to 50 kD, 250D and 50 KD, or 150 to 400 D.

9. The method according to claim 1, wherein the peritoneal therapeutic fluid further comprises at least one saccharide, and wherein the at least one saccharide is present in a total concentration of ≤0.02% by weight (200 mg/L), ≤0.75% by weight, ≤2.4% by weight, ≤5% by weight, ≤7.5% by weight, or ≤20% by weight.

10. The method according to claim 1, wherein the peritoneal therapeutic fluid is used for decreasing expression of Vascular Endothelial Growth Factor (VEGF) in the peritoneum.

11. The method according to claim 1, wherein the peritoneal therapeutic fluid is used for decreasing long term fibrosis.

12. The method according to claim 1, wherein the biocompatibility enhancing agent is pegylated with Polyethyleneglycol (PEG) or Methoxy-Polyethyleneglycol (mPEG), provided that the BCA is not polyethylene glycol (PEG) or a derivative of a polyethylene glycol.

13. The method according to claim 1, wherein the peritoneal therapeutic fluid further comprises at least one ingredient which is selected from the group consisting of alkali metal ions, alkaline earth metal ions, an osmotic agent and a pH-buffer.

14. The method according to claim 1, wherein the peritoneal therapeutic fluid further comprises at least one osmotic agent.

15. The method according to claim 1, wherein the peritoneal therapeutic fluid further comprises glucose.

16. The method according to claim 1, wherein the peritoneal therapeutic fluid further comprises a saccharide selected from the group consisting of fructose, a disaccharide, an oligosaccharide, maltodextrin and a polysaccharide, or any combination thereof.

17. The method according to claim 1, wherein the biocompatibility enhancing agent is resveratrol.

18. The method according to claim 1, wherein the peritoneal therapeutic fluid is an aqueous solution has an alkali equivalent in an amount of 25 to 50 mEq/L.

19. The method according to claim 1, wherein the electrolytes comprise one or more of sodium, potassium, calcium, and/or magnesium.

20. A method comprising administering to a human patient a peritoneal therapeutic fluid, the peritoneal therapeutic fluid comprising at least one biocompatibility enhancing agent (BCA), wherein the BCA is a resveratrol derivative, to conduct peritoneal dialysis on the human patient, wherein cytotoxicity on human peritoneal mesothelial cells is decreased compared to other peritoneal therapeutic fluids that do not contain the BCA, wherein the at least one BCA is present in a concentration of between 0.05 to 20 μMol/L, wherein the peritoneal therapeutic fluid comprises electrolytes, and wherein the resveratrol derivative is a compound of formula 2 or 8:

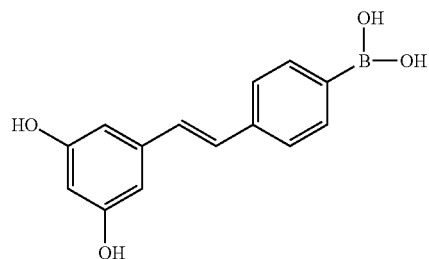

1

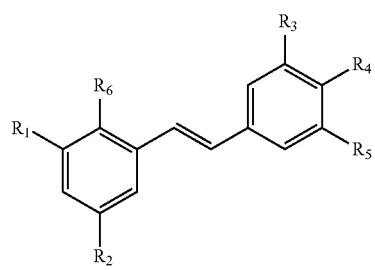

2

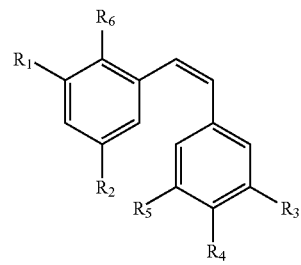

3

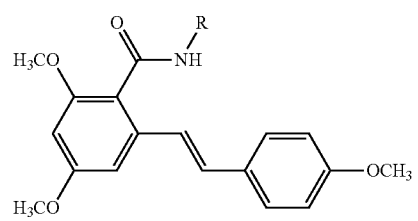

4

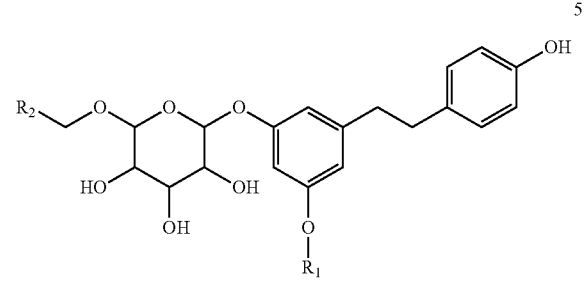

5

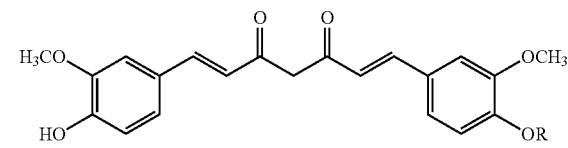

6

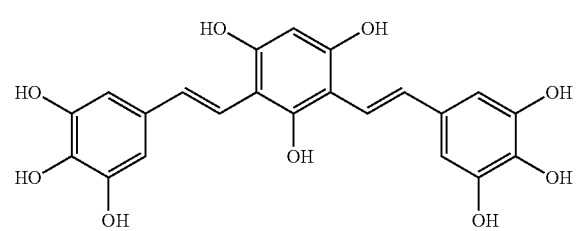

7

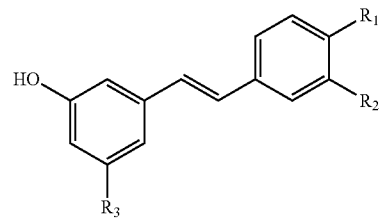

8

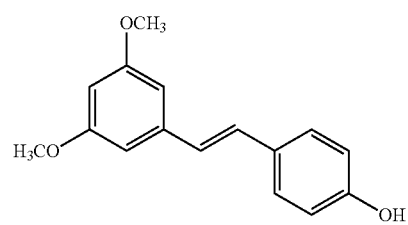

9

-continued

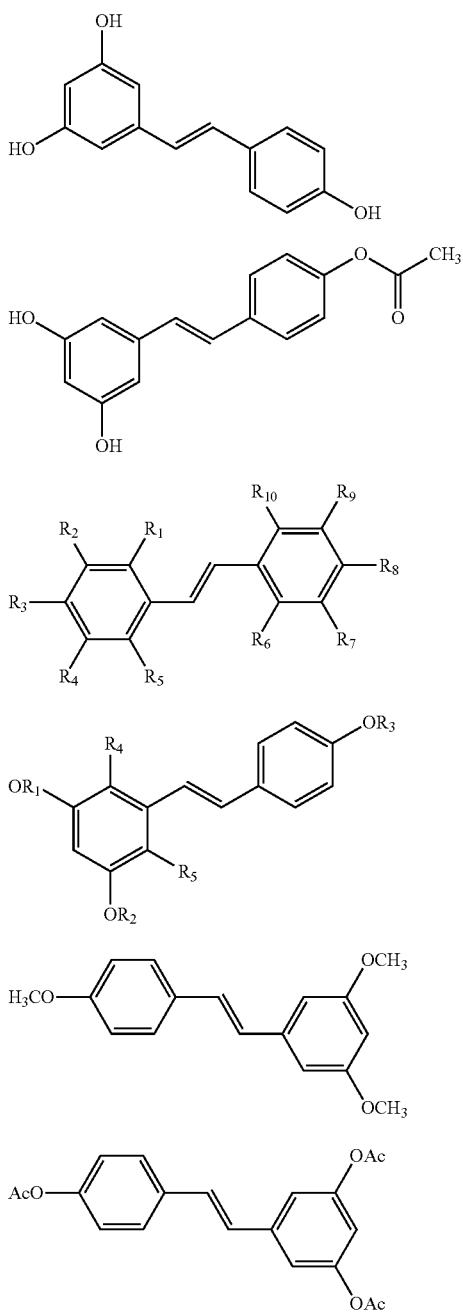

wherein in compound 2
R1=R2=R4=OCH3, R3=R5=R6=H; or
R1=R2=R3=R5=OCH3, R4=R6=H; or
R1=R2=R3=R4=OCH3, R5=R6=H, and
wherein in compound 8
R1=OCH3, R2=OH, R3=O-Glucose; or
R1=OCH3, R2=H, R3=O-Glucose; or
R1=OCH3, R2=OH, R3=OH; or
R1=OCH3, R2=H, R3=OH; or
R1=OH, R2=OH, R3=O-Glucose.

21. A method comprising administering to a human patient a peritoneal therapeutic fluid, the peritoneal therapeutic fluid comprising at least one biocompatibility enhancing agent (BCA), wherein the BCA is a resveratrol derivative, to conduct peritoneal dialysis on the human patient, wherein cytotoxicity on human peritoneal mesothelial cells is decreased compared to other peritoneal therapeutic fluids that do not contain the BCA,
wherein the at least one BCA is present in a concentration of between 0.05 to 20 μMol/L,
wherein the peritoneal therapeutic fluid comprises electrolytes, and
wherein the resveratrol derivative is a compound of formula 19:

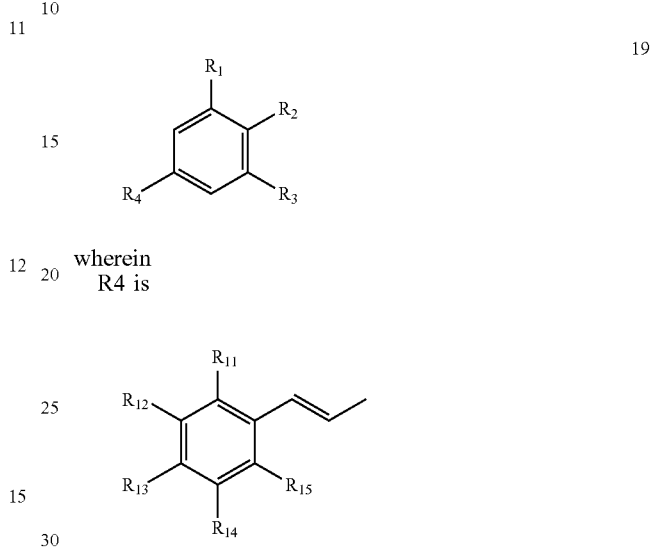

wherein
R4 is wherein R1, R2, R3, R11, R12, R13, R14, and R15 are independently from each other selected from
—H, —OH, —O—$R_{Alk}$, —CHO, —COR$_{Alk}$, —COOH, —COO—R$_{Alk}$,  —CO—NH—$C_nH_{2n}$—COOH, —CO—NH—$C_nH_{2n}$—COO,
—CN, —Cl, —Br, —I, —NO$_2$, —$C_nH_{2n}$CN, —$C_nH_{2n}$—Cl, —$C_nH_{2n}$—Br, —$C_nH_{2n}$—I, —$C_nH_{2n}$—NO$_2$,
—O—PO$_3^{2-}$, —O—PO$_3$H$^-$, —O—PO$_3$H$_2$, —NH$_2$, —NHR$_{Alk}$, —NR$_{Alk1}$R$_{Alk2}$, —N$^+$H$_3$, —N$^+$H$_2$R$_{Alk}$, —N$^+$HR$_{Alk1}$,R$_{Alk2}$, —N$^+$ R$_{Alk1}$,R$_{Alk2}$R$_{Alk3}$,
—B(OH)$_2$, —OCHO, —O—COR$_{Alk}$, —OCF$_3$, —O—CN, —OCH$_2$CN,
wherein R$_{Alk}$, R$_{Alk1}$, R$_{Alk2}$, and R$_{Alk3}$ are alkyl residues which are independently selected from each other, wherein the alky residues are CH$_3$, C$_2$H$_5$, C$_3$H$_7$ or C$_4$H$_9$, and
wherein $C_nH_{2n}$ is CH$_2$, C$_2$H$_4$, C$_3$H$_6$, or C$_4$H$_8$.

22. The method according to claim 20, wherein the peritoneal therapeutic fluid is an aqueous solution comprising:
sodium in an amount of 90 to 150 mEq/L;
potassium in an amount of 0 to 5 mEq/L;
calcium in an amount of 0 to 6 mEq/L;
magnesium in an amount of 0 to 4 mEq/L; and
an alkali equivalent in an amount of 25 to 50 mEq/L.

23. The method according to claim 20, wherein the peritoneal therapeutic fluid further comprises at least one saccharide.

24. The method according to claim 20, further comprising at least one disaccharide selected from the group consisting of sucrose, Gentiobiulose, Laminaribiose, Gentiobiose, Rutinulose, Xylobiose, trehalose, β,β-Trehalose, α,β-Trehalose, lactulose, sophorose, lactose, cellobiose, chitobiose, maltose, Kojibiose, Nigerose, Isomaltose, Turanose, Maltulose, Palatinose, Mannobiose, Melibiose, Melibiulose, and Rutinose.

25. The method according to claim 20, wherein the peritoneal therapeutic fluid further comprises maltodextrin or at least one oligosaccharide that is a product of limited hydrolysis of one of more of the following: starch, amylose, amylopectin, fructan, glucan, galactan, mannan, cellulose, arabic gum, glycogen, dextran, hemicellulose, arabinoxylose, and pectin, wherein the product of limited hydrolysis has a molecular weight of 90 D to 500 kD.

26. The method according to claim 20, wherein the peritoneal therapeutic fluid further comprises at least one alpha-glucan with a degree of polymerization of 3 or higher and has a molecular weight of 90 D to 500 kD.

27. The method according to claim 20, wherein the peritoneal therapeutic fluid further comprises at least one saccharide which is selected from the group consisting of isomaltotriose, nigerotriose, maltotriose, melezitose, maltotriulose, raffinose, kestose, maltodextrin, dextrins, heparin, Dextran, glycogen, pullulan, starch, amylose, amylopectin, icodextrin, and combinations thereof.

28. The method according to claim 20, wherein the peritoneal therapeutic fluid further comprises at least one saccharide which has a molecular weight in a range of 90D to 50 kD, 90D to 500 D, 90D to 1.5 kD, 1.5 kD to 50 kD, 350D to 50 kD, 250D and 50 KD, or 150 to 400 D.

29. The method according to claim 20, wherein the peritoneal therapeutic fluid further comprises at least one saccharide, and wherein the at least one saccharide is present in a total concentration of ≥0.02% by weight (200 mg/L), ≥0.75% by weight, ≥2.4% by weight, ≥5% by weight, ≥7.5% by weight, or ≥20% by weight.

30. The method according to claim 20, wherein the peritoneal therapeutic fluid is used for decreasing expression of Vascular Endothelial Growth Factor (VEGF) in the peritoneum.

31. The method according to claim 20, wherein the peritoneal therapeutic fluid is used for decreasing long term fibrosis.

32. The method according to claim 20, wherein the biocompatibility enhancing agent is pegylated with Polyethyleneglycol (PEG) or Methoxy-Polyethyleneglycol (mPEG), provided that the BCA is not polyethylene glycol (PEG) or a derivative of a polyethylene glycol.

33. The method according to claim 20, wherein the peritoneal therapeutic fluid further comprises at least one ingredient which is selected from the group consisting of alkali metal ions, alkaline earth metal ions, an osmotic agent and a pH-buffer.

34. The method according to claim 20, wherein the peritoneal therapeutic fluid further comprises at least one osmotic agent.

35. The method according to claim 20, wherein the peritoneal therapeutic fluid further comprises glucose.

36. The method according to claim 20, wherein the peritoneal therapeutic fluid further comprises a saccharide selected from the group consisting of fructose, a disaccharide, an oligosaccharide, maltodextrin and a polysaccharide, or any combination thereof.

37. The method according to claim 20, wherein the peritoneal therapeutic fluid is an aqueous solution has an alkali equivalent in an amount of 25 to 50 mEq/L.

38. The method according to claim 20, wherein the electrolytes comprise one or more of sodium, potassium, calcium, and/or magnesium.

39. The method according to claim 21, wherein the peritoneal therapeutic fluid is an aqueous solution comprising:

sodium in an amount of 90 to 150 mEq/L;
potassium in an amount of 0 to 5 mEq/L;
calcium in an amount of 0 to 6 mEq/L;
magnesium in an amount of 0 to 4 mEq/L; and
an alkali equivalent in an amount of 25 to 50 mEq/L.

40. The method according to claim 21, wherein the peritoneal therapeutic fluid further comprises at least one saccharide.

41. The method according to claim 31, further comprising at least one disaccharide selected from the group consisting of sucrose, Gentiobiulose, Laminaribiose, Gentiobiose, Rutinulose, Xylobiose, trehalose, β,β-Trehalose, α,β-Trehalose, lactulose, sophorose, lactose, cellobiose, chitobiose, maltose, Kojibiose, Nigerose, Isomaltose, Turanose, Maltulose, Palatinose, Mannobiose, Melibiose, Melibiulose, and Rutinose.

42. The method according to claim 21, wherein the peritoneal therapeutic fluid further comprises maltodextrin or at least one oligosaccharide that is a product of limited hydrolysis of one of more of the following: starch, amylose, amylopectin, fructan, glucan, galactan, mannan, cellulose, arabic gum, glycogen, dextran, hemicellulose, arabinoxylose, and pectin, wherein the product of limited hydrolysis has a molecular weight of 90 D to 500 kD.

43. The method according to claim 21, wherein the peritoneal therapeutic fluid further comprises at least one alpha-glucan with a degree of polymerization of 3 or higher and has a molecular weight of 90 D to 500 kD.

44. The method according to claim 21, wherein the peritoneal therapeutic fluid further comprises at least one saccharide which is selected from the group consisting of isomaltotriose, nigerotriose, maltotriose, melezitose, maltotriulose, raffinose, kestose, maltodextrin, dextrins, heparin, Dextran, glycogen, pullulan, starch, amylose, amylopectin, icodextrin, and combinations thereof.

45. The method according to claim 21, wherein the peritoneal therapeutic fluid further comprises at least one saccharide which has a molecular weight in a range of 90D to 50 kD, 90D to 500 D, 90D to 1.5 kD, 1.5 kD to 50 kD, 350D to 50 kD, 250D and 50 KD, or 150 to 400 D.

46. The method according to claim 21, wherein the peritoneal therapeutic fluid further comprises at least one saccharide, and wherein the at least one saccharide is present in a total concentration of ≥20.02% by weight (200 mg/L), ≥0.75% by weight, ≥2.4% by weight, ≥5% by weight, ≥7.5% by weight, or ≥20% by weight.

47. The method according to claim 21, wherein the peritoneal therapeutic fluid is used for decreasing expression of Vascular Endothelial Growth Factor (VEGF) in the peritoneum.

48. The method according to claim 21, wherein the peritoneal therapeutic fluid is used for decreasing long term fibrosis.

49. The method according to claim 21, wherein the biocompatibility enhancing agent is pegylated with Polyethyleneglycol (PEG) or Methoxy-Polyethyleneglycol (mPEG), provided that the BCA is not polyethylene glycol (PEG) or a derivative of a polyethylene glycol.

50. The method according to claim 21, wherein the peritoneal therapeutic fluid further comprises at least one ingredient which is selected from the group consisting of alkali metal ions, alkaline earth metal ions, an osmotic agent and a pH-buffer.

51. The method according to claim 21, wherein the peritoneal therapeutic fluid further comprises at least one osmotic agent.

52. The method according to claim 21, wherein the peritoneal therapeutic fluid further comprises glucose.

53. The method according to claim 21, wherein the peritoneal therapeutic fluid further comprises a saccharide selected from the group consisting of fructose, a disaccharide, an oligosaccharide, maltodextrin and a polysaccharide, or any combination thereof.

54. The method according to claim 21, wherein the peritoneal therapeutic fluid is an aqueous solution has an alkali equivalent in an amount of 25 to 50 mEq/L.

55. The method according to claim 21, wherein the electrolytes comprise one or more of sodium, potassium, calcium, and/or magnesium.

\* \* \* \* \*